United States Patent
Yoshimura et al.

(10) Patent No.: US 6,169,780 B1
(45) Date of Patent: Jan. 2, 2001

(54) X-RAY APPARATUS WITH IMPROVED PATIENT ACCESS

(75) Inventors: Takahiro Yoshimura; Masanobu Yoshida; Masanori Otsuka, all of Kyoto (JP)

(73) Assignee: J. Morita Manufacturing Corp., Kyoto (JP)

(*) Notice: Under 35 U.S.C. 154(b), the term of this patent shall be extended for 0 days.

(21) Appl. No.: 09/161,777

(22) Filed: Sep. 29, 1998

(30) Foreign Application Priority Data

Sep. 30, 1997 (JP) .................................................. 9-267042
Sep. 30, 1997 (JP) .................................................. 9-267204
Sep. 30, 1997 (JP) .................................................. 9-267207

(51) Int. Cl.[7] .............................. H04N 5/32; A61B 6/14
(52) U.S. Cl. ................................. 378/39; 378/38; 378/40
(58) Field of Search ................................. 378/38, 39, 40, 378/21, 23, 25, 208, 167, 168, 177, 180, 181

(56) References Cited

U.S. PATENT DOCUMENTS

| | | |
|---|---|---|
| 4,039,837 | 8/1977 | Ohta et al. . |
| 4,365,340 * | 12/1982 | Nishikawa et al. ................... 378/19 |
| 4,418,419 | 11/1983 | Schreiber et al. . |
| 4,675,888 | 6/1987 | Gastrin . |
| 4,783,793 | 11/1988 | Virta et al. . |
| 4,985,907 | 1/1991 | Moteni . |
| 5,016,264 | 5/1991 | Hyttinen . |
| 5,058,147 | 10/1991 | Nishikawa et al. . |
| 5,224,140 | 6/1993 | Virta et al. . |
| 5,500,884 | 3/1996 | Guenther et al. . |
| 5,921,927 * | 7/1999 | McArdle ............................ 378/39 X |

FOREIGN PATENT DOCUMENTS

| | | |
|---|---|---|
| 60-137352 | 7/1985 | (JP) . |
| 63-14816 | 4/1988 | (JP) . |
| 03082453 | 4/1991 | (JP) . |
| 06022954 | 2/1994 | (JP) . |

* cited by examiner

*Primary Examiner*—David P. Porta
(74) *Attorney, Agent, or Firm*—Pillsbury Madison & Sutro LLP

(57) ABSTRACT

An X-ray device for generating a panoramic tomogram is designed so that a revolving arm can move between a first position, where an X-ray generator and an X-ray receiver that are both supported by the revolving arm oppose each other through the head of a patient positioned in a patient positioning station, and a second position, where an operator of the X-ray device can look at the patient's head from a side view, thereby allowing the operator to properly position the patient in the patient positioning station. The incorporation of a second X-ray receiver additionally allows for the generation of a cephalogram. The incorporation of a blind prevents the patient from visually or physically interacting with selected components of the apparatus.

29 Claims, 28 Drawing Sheets

X-RAY APPARATUS WITH IMPROVED PATIENT ACCESS

BACKGROUND OF THE INVENTION

1. Field of Invention

The present invention relates to an X-ray apparatus and more particularly to dental X-ray apparatus for generating a panoramic tomogram.

2. Description of Related Art

X-ray devices commonly used in medical and dental applications are limited by their ability to accommodate patients and operators while carrying out technical operations. On one hand, the apparatus must be capable of carrying out detailed translations and rotations of the X-ray source and receiver. However, achieving this in a physically confined space can lead to other problems. Components of the apparatus may impede patient access to and from the patient positioning area and may also obscure a necessary view of the patient by an operator of the apparatus. The patient's ability to view components of the apparatus in operation can lead to patient anxiety and distraction. Furthermore, the patient's ability to interact physically with components of the apparatus can endanger both the patient and the apparatus.

U.S. Pat. No. 4,039,837 issued to the present applicant on Apr. 2, 1977, discloses a dental X-ray apparatus that includes a first frame, a pivot or revolving shaft extending substantially vertically from the first frame, an X-ray generator, an X-ray receiver and a second frame supported substantially at a central portion thereof on the revolving shaft for supporting the X-ray generator and X-ray receiver with a predetermined space therebetween. The first frame is equipped with an X/Y-transport mechanism which allows the second frame to move in all horizontal directions relative to the first frame.

The X/Y-transport mechanism includes a pair of parallel rails (Y-rails) extending horizontally in a certain direction (Y-direction) and spaced apart from each other, a Y-platform with an opening movably supported on the Y-rails, and a Y-motor with a drive for moving the Y-platform in the Y-direction. Also, the X/Y-transport mechanism has a pair of parallel rails (X-rails) extending in a direction (X-direction) perpendicular to the Y-direction and mounted on the Y-platform, an X-platform movably supported on the X-rails, and an X-motor with a drive for moving the X-platform in the X-direction. The revolving shaft, which is supported at an upper end thereof on the X-platform so that it can rotate about a longitudinal axis thereof, is extended downward through the opening of the Y-platform and then fixedly connected to the second frame at a lower end thereof. The revolving shaft is also connected with a drive to a shaft-motor mounted on the X-platform so that it can rotate about its longitudinal axis.

In operation of the X-ray apparatus, the revolving shaft rotates about its longitudinal axis when driven by the corresponding motor. Further, by means of the X-motor and the Y-motor, the revolving shaft along with the second frame supported on the revolving shaft is permitted to move to a required position within a range in which the X-platform and the Y-platform can move. Therefore, for example, a panoramic radiogram of a dentition or dental arch can be executed by rotating the X-ray generator and X-ray receiver. In this operation, an X-ray beam emitted from the X-ray generator toward the X-ray receiver is kept substantially perpendicular to the dentition. Also, a photosensitive film supported in the X-ray receiver is displaced in a direction opposite to a rotational direction of the X-ray generator in synchrony with a velocity of the X-ray scanning along the dentition.

As discussed above, operational difficulties can occur during patient interaction with such an apparatus. These problems result from undesirable visual as well as physical contact between the apparatus and the patient or the operator.

SUMMARY OF THE INVENTION

Accordingly, it is an object of this invention to provide an improved X-ray apparatus having an X/Y-transport mechanism and a shaft rotation mechanism as described above for carrying out detailed motions of an X-ray generator and an X-ray receiver in the generation of a panoramic tomogram.

It is a further object of this invention to provide an X-ray apparatus that allows an operator to suitably position a patient with respect to the apparatus with an aid of the X/Y-transport mechanism.

It is a further object of this invention to provide an X-ray apparatus that allows a patient to readily approach a predetermined positioning station with an aid of the X/Y-transport mechanism.

It is a further object of this invention to provide an X-ray apparatus with a cephalostat which occupies a relatively small space.

It is a further object of this invention to provide an X-ray apparatus suitable for generating in a linear tomogram.

It is a further object of this invention to provide and X-ray apparatus that includes a mechanism that separates a patient from selected mechanical structures (e.g., X/Y-transport mechanism) incorporated into the apparatus.

The above and related objects of the present invention are realized by providing a system that comprises a first frame that includes a support and a patient positioning station spaced apart from the support. The support carries a transport mechanism that includes a first guide extending in a first direction, a first moving member movably supported on the first guide, and a first drive for moving the first moving member along the first guide. The apparatus further has a second frame that includes a second guide fixed on the first moving member and extended in a second direction which crosses the first direction at a certain angle (e.g., 90 degrees), a second moving member movably supported on the second guide, and a second drive for moving the second moving member along the second guide. A revolving shaft is connected with the second moving member at one end thereof and with the second frame at the other end thereof. The second frame includes an X-ray generator having an X-ray source and a X-ray receiver having an X-ray receiving surface that is spaced apart from the X-ray generator. Also, the second frame is connected at a portion thereof located between the X-ray generator and receiver with the other end of the revolving shaft. A revolving mechanism includes a drive source (e.g., motor) that allows the second frame to revolve relative to the first frame about the revolving shaft. Operations of the transport mechanism and the pivot mechanism are controlled by means of digital signals transmitted from a controller.

In another aspect of the present invention, in addition to the above mentioned construction, the transport mechanism is designed so that the second frame moves between a first position where the X-ray generator faces the X-ray receiver through the head of a patient positioned in the patient positioning station and a second position where the X-ray generator and the X-ray receiver are displaced so that an operator of the apparatus can diagonally view the face of the patient positioned in the patient positioning station. Then, by setting the second frame in the second position, the operator can guide the patient into the suitable position while facing a front or oblique view of the patient.

In another aspect of the present invention, the transport mechanism is so designed that the second frame can move between a first position where the X-ray generator faces the X-ray receiver through the head of a patient positioned in the patient positioning station and a second position where an area located between the X-ray generator and X-ray receiver is substantially out of the head of patient positioned in the patient positioning station. Then, by setting the second frame in the second position, the patient can approach the patient positioning station without any interference from the second frame. In addition, the operator can suitably position the patient while facing the face of the patient without any interference from the second frame.

In another aspect of the present invention, the first frame includes a first portion extending in a certain direction and a second portion extending from one end of the first portion in a direction that crosses at a certain angle (e.g., 45 degrees). In addition, the transport mechanism is incorporated into the second portion. With this arrangement, the patient can be guided to the patient positioning station more easily, and the operator can properly position the patient more readily.

In another aspect of the present invention, the apparatus includes a second X-ray receiving surface for use in a cephalogram, where this surface is mounted either on a revolving arm spaced away therefrom and connected mechanically with the first frame or on a second X-ray receiver independently supported on a wall without any mechanical connection with the first frame. The apparatus then also includes a displacing mechanism for displacing the first X-ray receiving surface from between the X-ray source and the second X-ray receiving surface, a mode selector for selecting a cephalogram mode in which the second X-ray receiving surface will be used or other tomographic modes in which the first X-ray receiving surface will be used, and a controller for moving the X-ray generator to a position where the X-ray can reach a maximum distance away from the second X-ray receiver with respect to the first or second direction. With this arrangement, the X-ray apparatus occupies relatively minimal space with respect to the first or second direction.

In another aspect of the present invention, the apparatus includes a rotating shaft extending parallel to the revolving shaft and connecting the X-ray receiver to the second frame for rotation about the rotating shaft, a motor mounted on the second frame, and a transmission connecting the rotation shaft to the motor for rotating the X-ray receiver relative to the second frame. With this arrangement, for example, in an operation of the linear tomogram, the X-ray receiving surface can be directed in any way as necessary during the rotational movement of the second frame.

In another aspect of the present invention, the apparatus includes a mechanism containing a blind that visually and mechanically separates the patient from an opening formed in the first frame through which the revolving shaft extends outwardly. In this instance, the patient is unable to view the mechanism incorporated in the first frame even when the revolving shaft is moving.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which.

DETAILED DESCRIPTION OF THE PRESENTLY PREFERRED EXEMPLARY EMBODIMENTS

Figure 1:
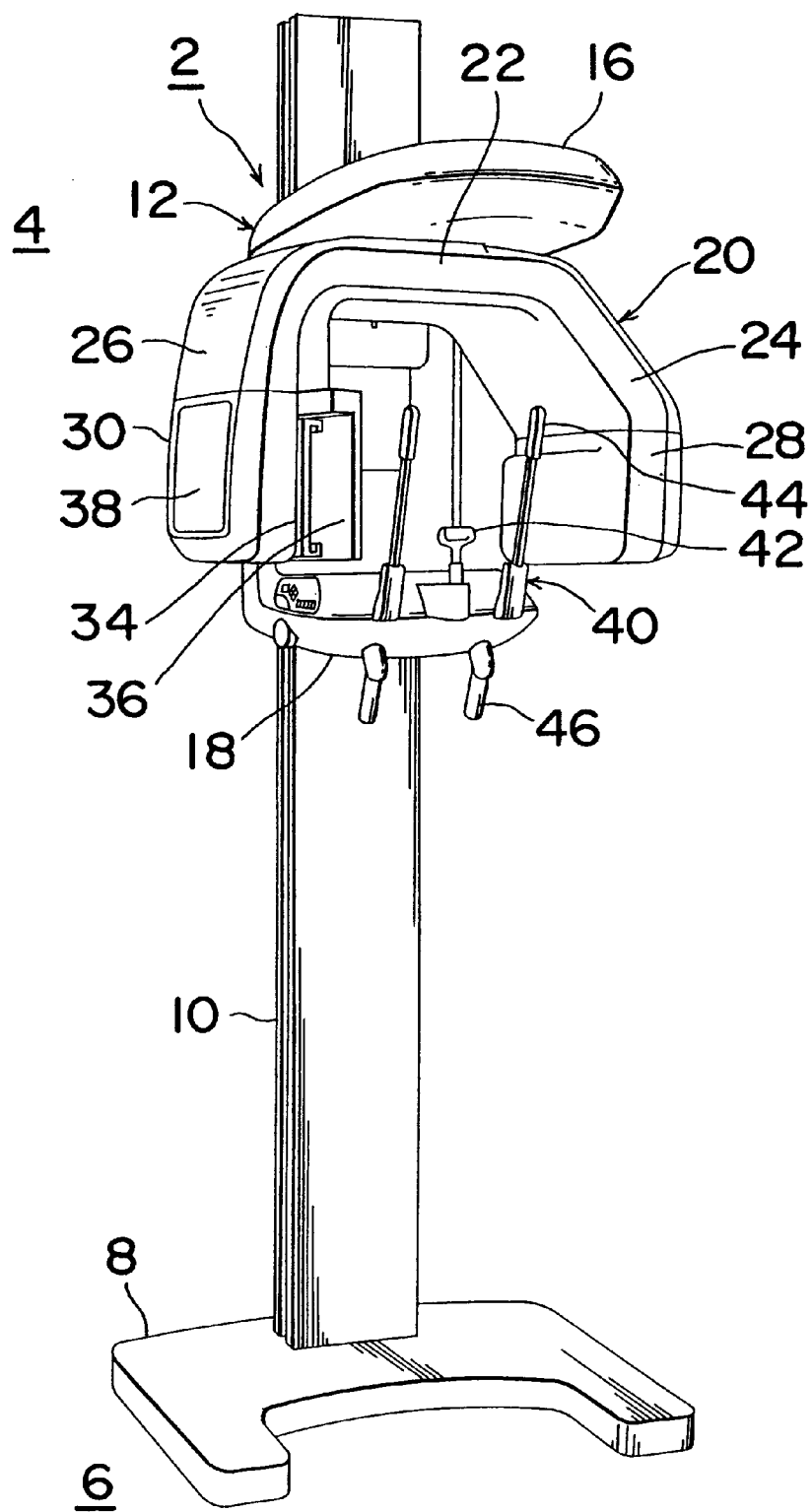
FIG. 1 is a perspective view of a first embodiment of an X-ray apparatus according to the present invention.
Figure 2:
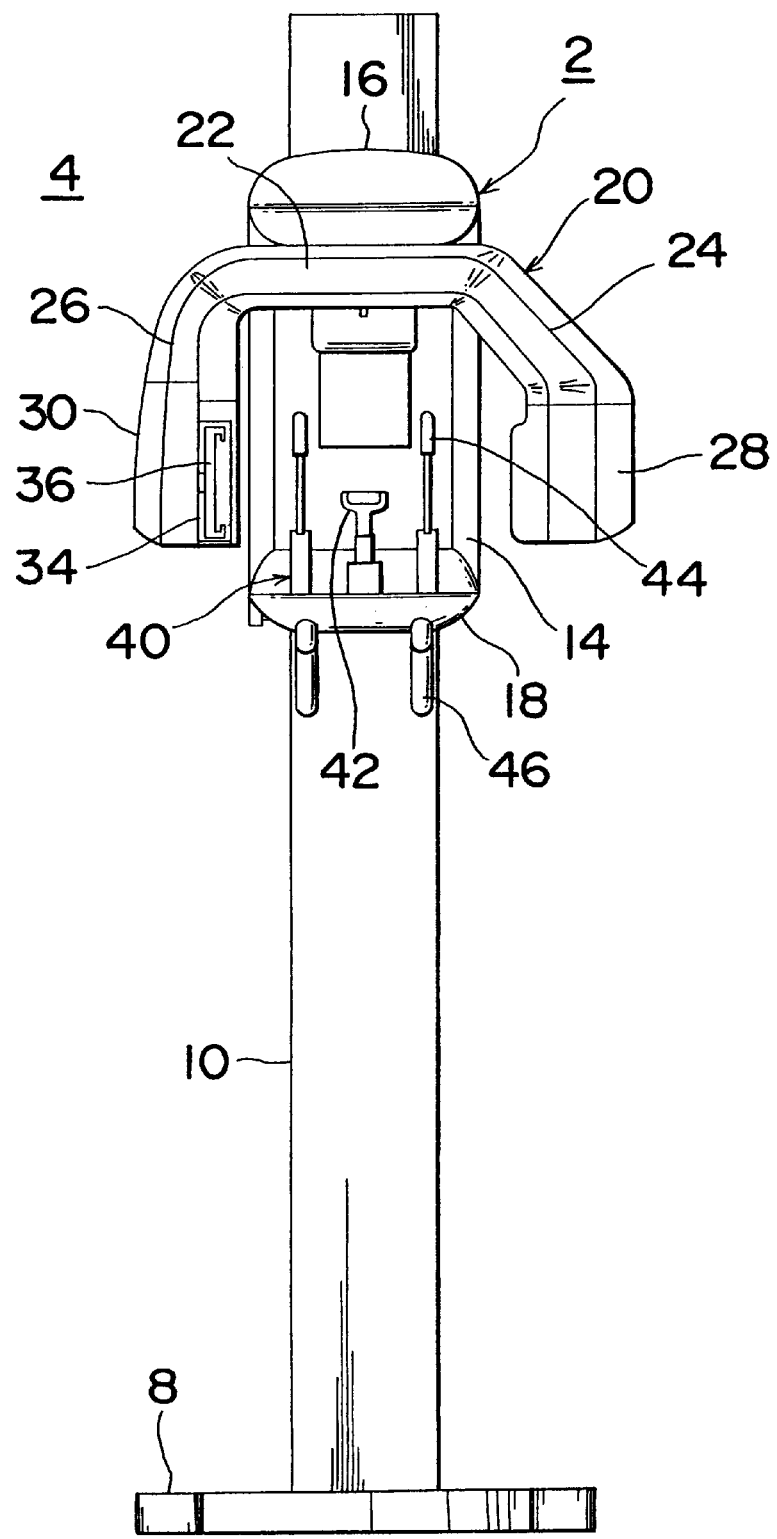
FIG. 2 is a front view of the X-ray apparatus shown in FIG. 1.
Figure 3:
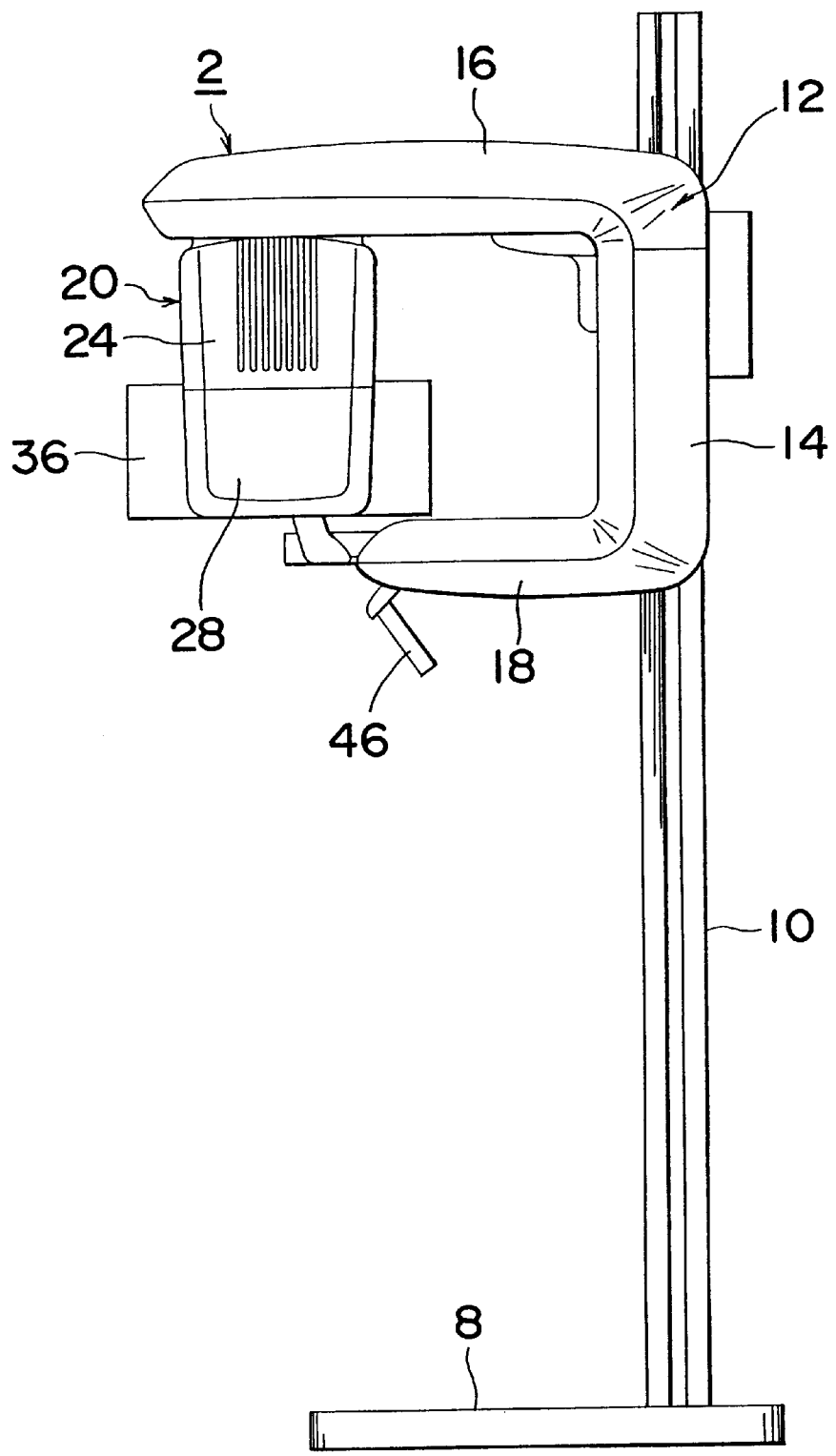
FIG. 3 is a right side view of the X-ray apparatus shown in FIG. 1.
Figure 4:
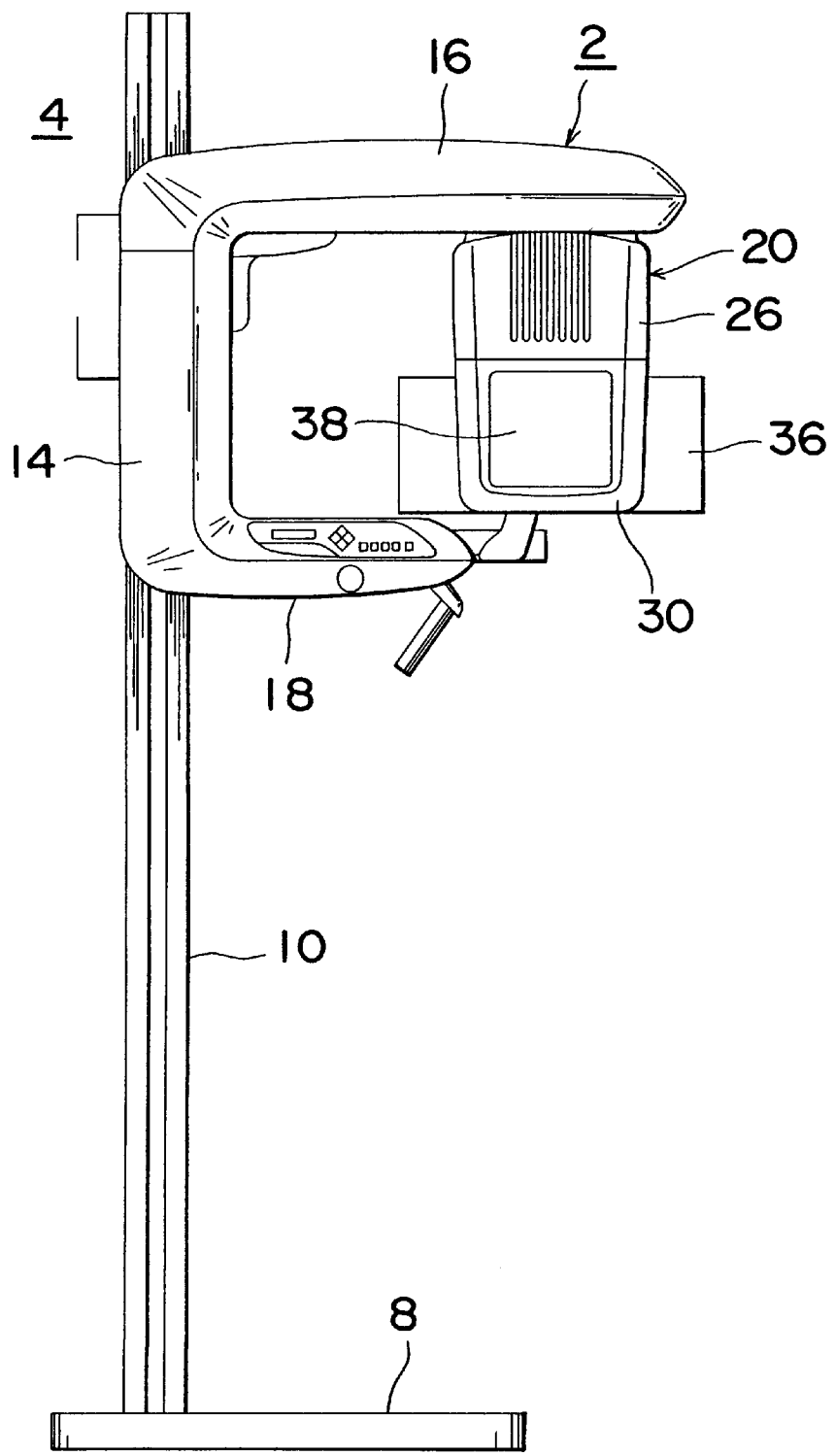
FIG. 4 is a left side view of the X-ray apparatus shown in FIG. 1.

Referring to the drawings, particularly in FIGS. 1 to 4, there is shown a first embodiment of a dental X-ray apparatus of the present invention, generally indicated by reference numeral 2. The X-ray device 2, which is typically installed in a chamber 4 suitably constructed for an X-ray tomography, includes a base plate 8 fixed on a floor 6 of the chamber 4, and a column 10 fixed at a bottom portion thereof on the base plate 8 and extended substantially vertically. The column 10 supports an elevation unit (first frame) 12 capable of moving up and down along the column 10. The elevation unit 12 integrally includes a substantially vertical portion 14 extending along the column 10, an upper portion (support) 16 extending substantially horizontally from an upper end of the vertical portion 14, and a lower portion 18 extending substantially horizontally and parallel to the upper portion 16.

Provided between the upper and lower portions 16 and 18 of the elevation unit 12 is a gate-like revolving arm (second revolving arm) 20 supported by the upper portion 16. The revolving arm 20 has a horizontal portion 22 running substantially horizontally below the upper portion 16, a portion 24 extended downwardly and outwardly from one end of the horizontal portion 22, a portion 26 also extended downwardly from the other end of the horizontal portion 22, an X-ray generator 28 mounted on a bottom of the former extended portion 24, and an X-ray receiver 30 mounted on a bottom of the latter extended portion 26. The X-ray generator 28 includes an X-ray source 32 (see FIG. 8) for emitting an X-ray beam toward the X-ray receiver 30. The X-ray receiver 30 is formed with a penetrating slot or through-hole (cassette holder 34) extending horizontally, inside a vertical wall adjacent to the X-ray generator 28. The cassette holder 34 releasably holds a cassette 36 having a X-ray receiving surface made of X-ray film or a number of CCD sensors which will be exposed to the X-ray beam transmitted from the X-ray generator 32. The X-ray receiver 30 includes an input 38 having switches on an opposite side thereof away from the X-ray generator 28 for selecting a required tomographic mode and for inputting various information.

Figure 5:
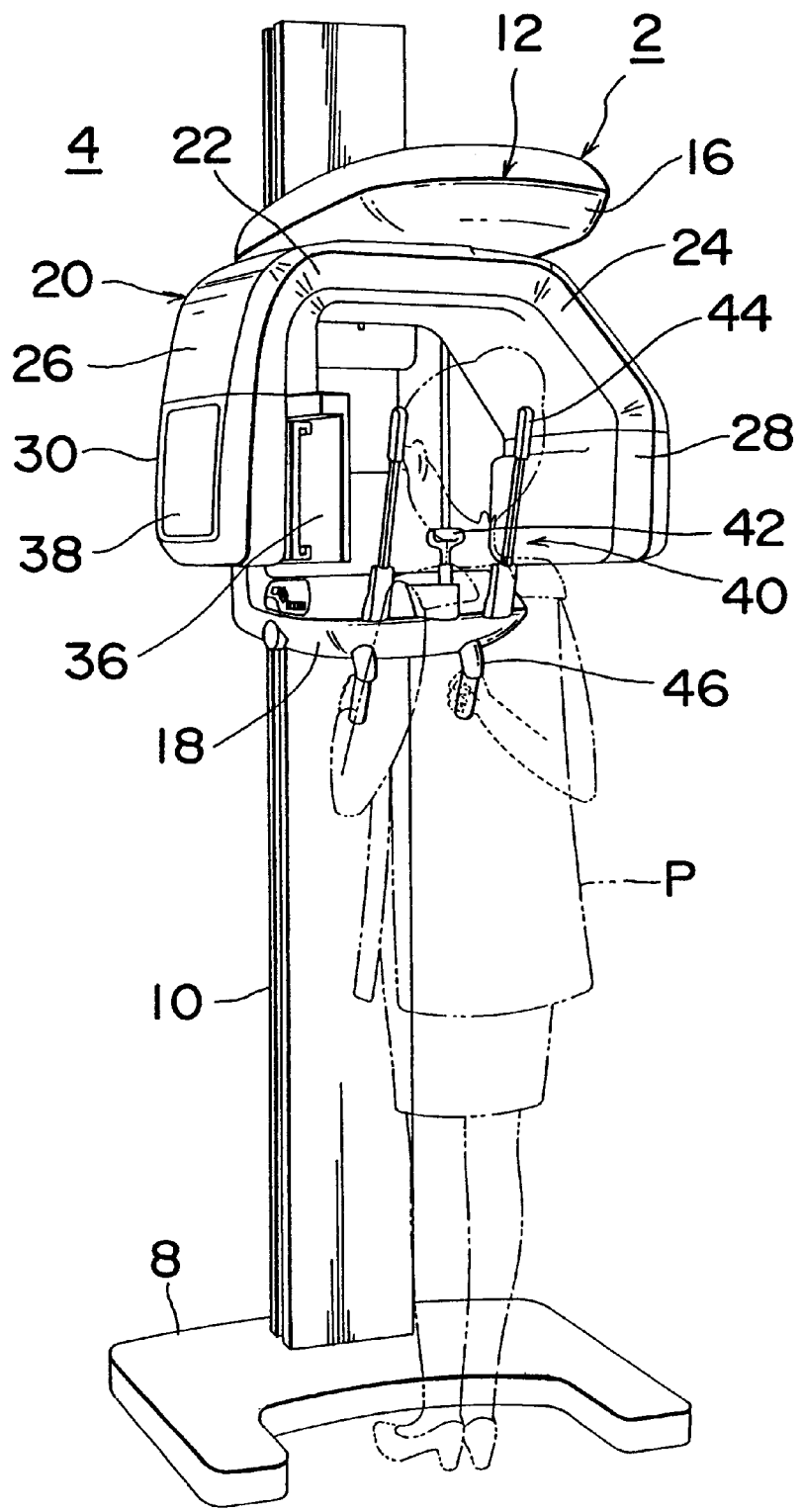
FIG. 5 shows a patient positioned in the X-ray apparatus shown in FIG. 1.

To suitably position the head of a patient to be photographed against the X-ray device 2, a positioning station 40 is provided on the lower portion 18 of the elevation unit 12. As shown in FIG. 5, the positioning station 40 includes a chin-rest 42 for the patient to rest his chin, a pair of restricting members 44 capable of being brought into contact with opposite sides of a head of the patient with his chin rested on the chin rest 42 to prevent the patient from moving laterally, a pair of handle bars 46 that the patient can hold at his positioning and photographing. It should be noted that the restricting members 44 are made of material having a minimum absorptance of X-rays.

Figure 6:
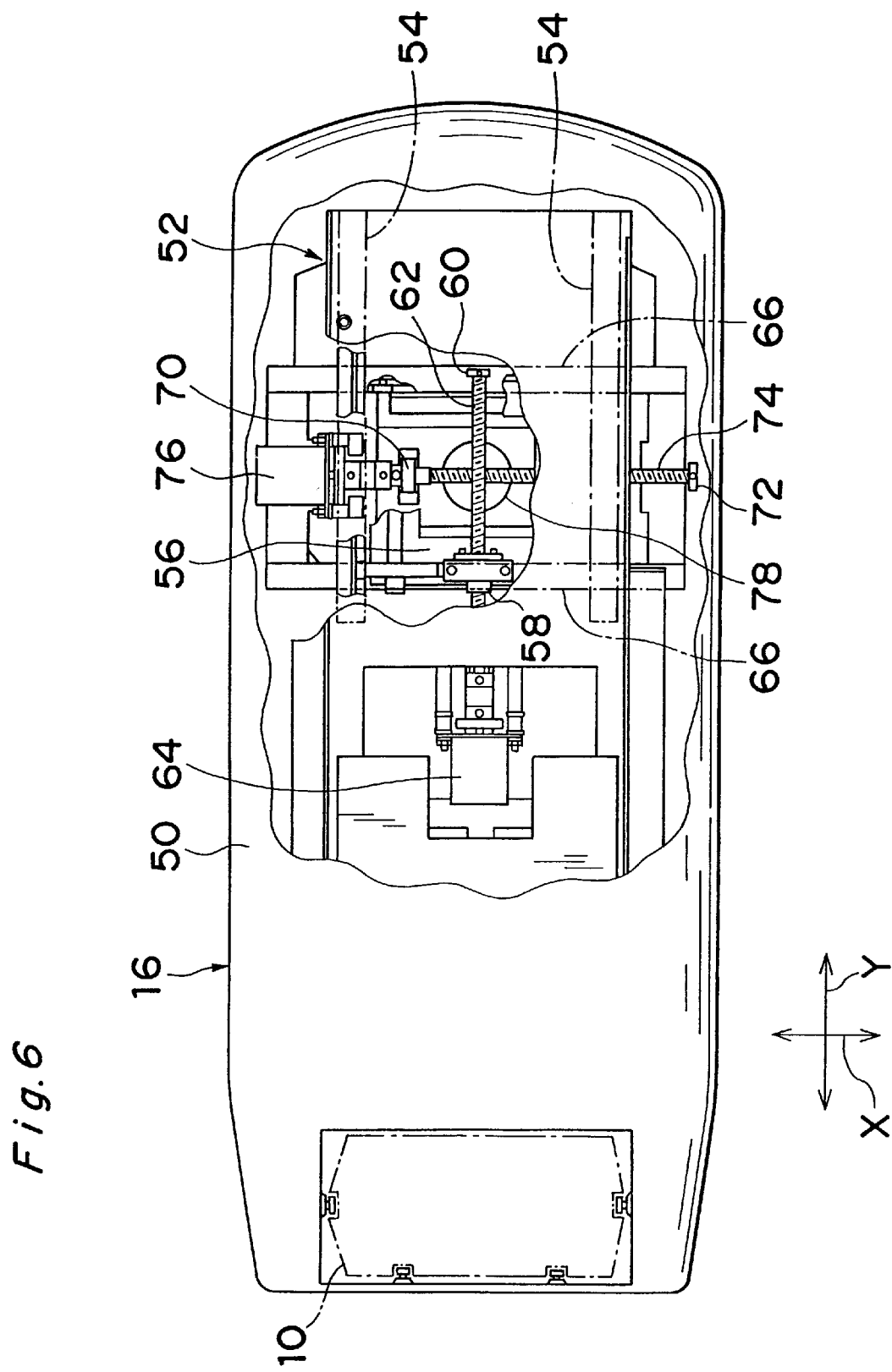
FIG. 6 is a partial cross-sectional plan view of an upper portion of an elevation unit of the X-ray apparatus shown in FIG. 1, showing a part of an X/Y-transport mechanism contained in the upper portion.
Figure 7:
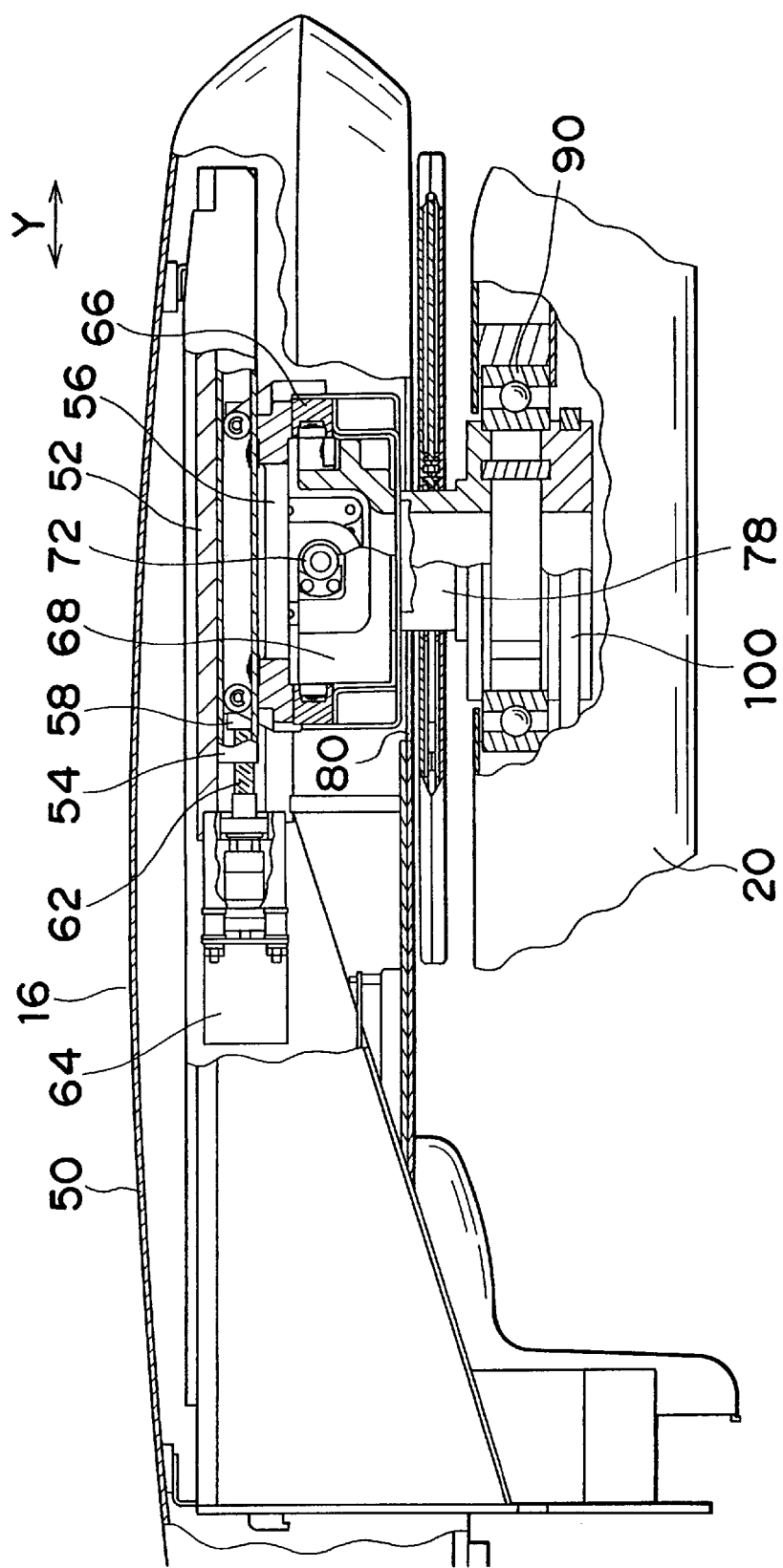
FIG. 7 is a partial cross-sectional side view of the upper portion of the elevation unit of the X-ray apparatus shown in FIG. 1, showing a part of an X/Y-transport mechanism contained in the upper portion.

FIGS. 6 and 7 illustrate an interior of the upper portion 16 of the elevation unit 12. The upper portion 16 has a housing 50, in which a transport mechanism (X/Y-transport mechanism) 52 is incorporated for moving the revolving arm 20 in a longitudinal direction (Y-direction) of the upper portion 16 and a transverse direction (X-direction) perpendicular to the Y-direction relative to the upper portion 16. The X/Y-transport mechanism 52 has a pair of parallel spaced Y-rails (first guide) 54 extending in the Y-direction and a Y-table 56 movably supported on the Y-rails 54. Two Y-nuts 58 and 60 are arranged on a line extending in the Y-direction and fixed on the Y-table 56. A Y-lead-screw is threaded in the Y-nuts 58 and 60, which lead screw being connected by a drive at one end thereof with a Y-motor (stepper motor) 64 secured on the housing 50. This results in that, upon rotation of the Y-lead-screw 62 clockwise and counterclockwise by the Y-motor 64, the Y-table 56 moves reciprocally along the Y-direction.

The X/Y-transport mechanism 52 includes a pair of X-rails (guide) 66 extending in the X-direction and spaced apart from each other. The X-rails 66 support a X-table 68 which moves along the X-rails 66. The X-table 68 carries two X-nuts 70 and 72 on a line extending in the X-direction, in which X-nuts 70 and 72 the X-lead-screw 74 is threaded. One end of the X-lead-screw 74 is connected by a drive with a X-motor (stepper motor) 76 so that, when the X-motor 76 is energized, the X-lead-screw 74 rotates clockwise and counterclockwise, thereby reciprocally moving the X-table 68 in the X-direction relative to the Y-table 56. To allow the transport mechanism 52 to support the revolving arm 20, the upper portion of the revolving shaft 78 is connected at the bottom of the X-table 68. The lower portion of the revolving shaft 78, on the other hand, is protruded through the opening 80 formed in the housing 50 toward the revolving arm 20.

Figure 8:
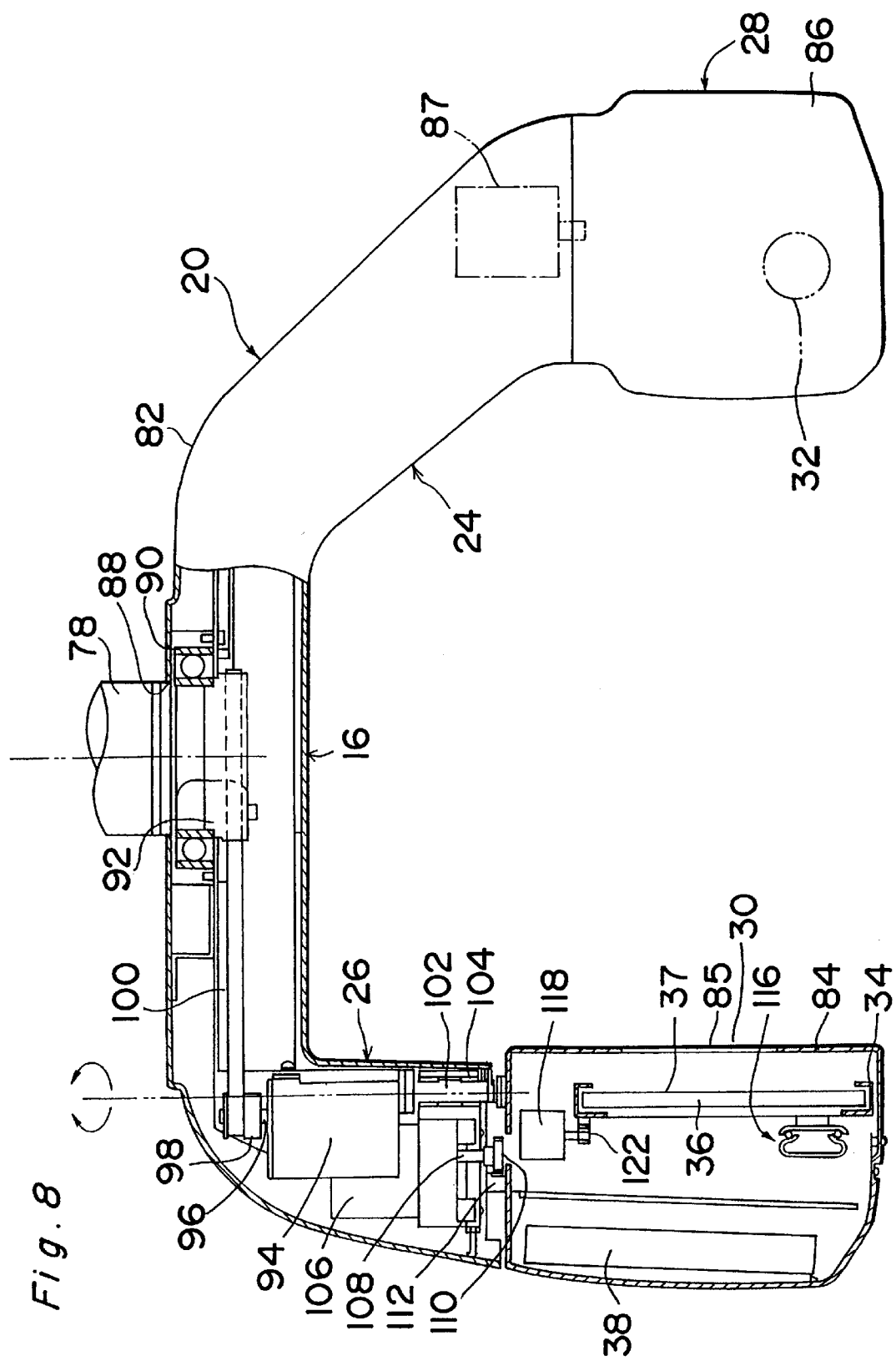
FIG. 8 is a partial cross-sectional side view of a revolving arm of the X-ray apparatus shown in FIG. 1, showing a mechanism contained in the revolving arm.

FIG. 8 shows a construction of the revolving arm 20 in which the extended portions 24 and 26 depending from opposite ends of the horizontal portion 16 are outlined by respective portions of the housing 82. The X-ray generator 28 and X-ray receiver 30 connected with the extended portions 24 and 26, respectively, are outlined by housings 84 and 86, respectively.

The housing 82 is formed at a central portion thereof with an opening 88 through which the lower end portion of the revolving shaft 78 is projected into an interior of the housing 82. To support the revolving shaft 78 so that it can rotate about a longitudinal axis thereof relative to the housing 82, a bearing 90 is provided inside the opening 88. The revolving shaft 78 carries a pulley 92 in coaxial relationship therewith. A motor 94, which is provided in the housing 82 for rotating the revolving arm 20 relative to the elevation unit 12, has an output shaft 96 on which a pulley 98 is secured. An endless belt 100 is entrained about the pulleys 92 and 98 so that the rotation of the output shaft 96 of the motor 94 can be transmitted through the pulley 98, belt 100, pulley 92 and then revolving shaft 78, rotating the revolving arm 20 about the revolving shaft 78.

Figure 9:
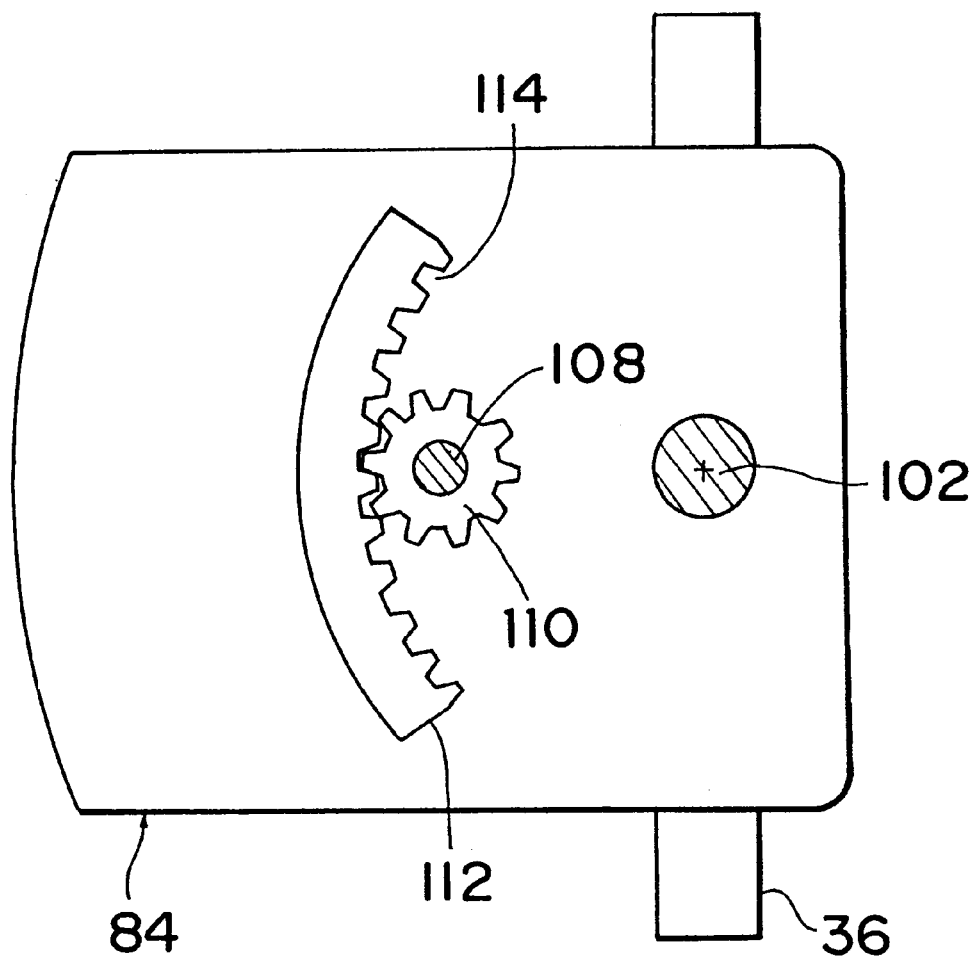
FIG. 9 is a plan view of a transmission for rotating a housing of an X-ray receiver relative to another housing of the revolving arm in the X-ray apparatus shown in FIG. 1.

Within a portion of the housing 82 forming the extended portion 26 adjacent the X-ray receiver 30, a shaft 102 is provided parallel to the revolving shaft 78 in the vicinity of a wall opposing to the X-ray generator 28. The shaft 102 is supported for rotation about a longitudinal axis thereof by a bearing 104 mounted in the housing 82. A lower end of the shaft 102 is connected with the housing 84 of the X-ray receiver 30, allowing the X-ray receiver 30 to revolve about the shaft 102. A drive source, i.e., motor (stepper motor) 106 for revolving the lower housing 84 relative to the main housing 82 is fixed in the housing 82 with an output shaft 108 directed downwardly and parallel to the revolving shaft 78. A gear 110 is fixed on the drive shaft 108. In addition, as shown in FIG. 9, an arch member 112 is mounted in an upper portion of the lower housing 84. The arch member 112 is formed with a rack 114 in an inner peripheral surface thereof which occupies a part of circle centered at the shaft 102. Also, the rack 114 is meshed with the gear 110. This ensures that, once the motor 106 is driven, a rotation of the drive shaft 108 is transmitted through the gear 110 and then rack 114, allowing the lower housing 84 to rotate relative to the upper housing 82.

As described above, the horizontally extended cassette guide 116 is formed in the housing 84, in which the cassette holder 34 for holding the cassette 36 is mounted with its X-ray receiving surface 37 confronted to the X-ray generator 28. A part of the housing 84 opposing the X-ray generator 28 is formed with a vertical slot 85 so that the X-ray receiving surface 37 of the cassette 36 can be exposed therethrough to the X-ray beam projected from the X-ray generator 32. To move the cassette 36 along the cassette holder 34 in synchrony with the rotation of the revolving arm 20, the housing 84 includes a motor (stepper motor) 118 and a transmission 122 which converts the rotation of the motor into a linear movement of the cassette 36 parallel to the longitudinal axis thereof. For example, the transmission 122 may be a mechanism which includes a gear fixed on the output shaft of the motor 118 and a rack mounted on the cassette 36 with which the gear engaged, or another mechanism which includes a roller, made of elastic material having a greater friction coefficient and fixed on the output shaft of the motor 118, with a peripheral surface thereof contacted with a surface of the cassette 36, for moving the cassette due to the rotation of the roller. In addition, the housing 84 has the input 38 in the side wall away from the X-ray generator 28.

Further, an X-ray source 32 is located in the housing 86 of the X-ray generator 28. In this embodiment, the housing 86 is fixedly connected with the main housing 82 of the revolving arm 20, however, the housing 86 may be independent of the main housing 82, similar to the housing 84 of the X-ray receiver 30. In this instance, it can be modified so that the motor (stepper motor) 87 is positioned in one housing 82 or 86 and an output shaft of the motor 87 is connected with the other housing 86, allowing the housing 86 to rotate relative to the main housing 82.

Figure 10:
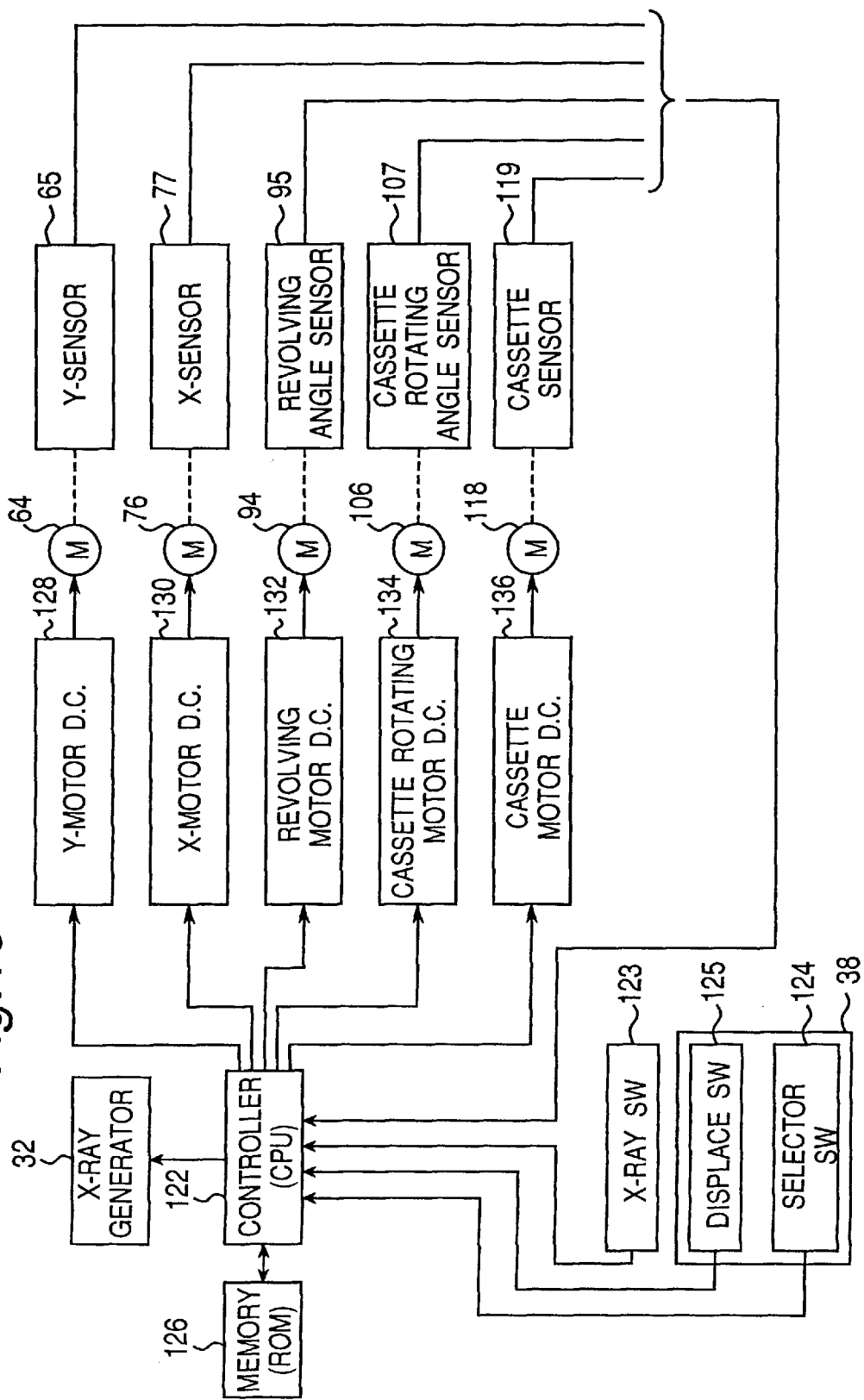
FIG. 10 is a control diagram of the X-ray apparatus shown in FIG. 1.

FIG. 10 shows a control circuit of the X-ray apparatus. The control circuit includes a controller 122 having a microcomputer. The controller 122 is electrically connected with the input 38, an X-ray emitting switch 123 and a memory 126. As described above, the input 38 mounted on the X-ray receiver 30 includes a tomographic mode selector 124 and a displacing switch 125. Examples of the tomographic modes that can be selected by the mode selector 124 are standard panoramic radiogram (magnification 1.3 or 1.7), pedondontic panoramic radiogram, maxillaly sinus panoramic radiogram (front or back), temporomandibular joint scanogram (quadruple), right angle panoramic radiogram, jaw panoramic radiogram, single side panoramic radiogram (left or right), jaw and arch cross sectional linear tomogram, jaw and arch parallel linear tomogram, maxillaly linear tomogram, temporomandibular joint linear tomogram, maxillaly sinus scanogram, temporomandibular joint scanogram, and facial skeleton linear projection.

The switch 125 is used to displace the revolving arm 20 from a starting position for the tomographic operation to a position displaced away from the starting position so that, prior to the photographic operation, the patient can readily approach the patient positioning station and/or the operator can easily observe the patient positioned at the positioning station.

The memory 126 stores control programs for respective tomographic modes and control data for various motors so that a signal corresponding to the tomographic mode selected at the input 38 is output to the controller 122, causing the various motors to drive according to the selected mode.

For motors 64, 76, 94, 106 and 118, the controller 122 includes a Y-motor drive circuit 128, an X-motor drive circuit 130, a revolving-arm-drive-motor drive circuit 132, a cassette-rotating-motor drive circuit 134, and a cassette-drive-motor drive circuit 136, respectively, so that each drive circuit transmits a digital signal to the corresponding motor in response to the signal fed from the controller 122. Sensors 65, 77, 95, 107 and 119 are positioned adjacent to respective paths of moving members which would be transported by the stepper motors 64, 76, 94, 106 and 118. This allows the controller to confirm whether each of the moving members is positioned at a predetermined initial position or has moved past it. For this purpose, the controller 122 is designed so that the signals made at respective sensors can be transmitted for suitable feedback control.

Operation of the X-ray apparatus 2 so constructed will be discussed below. Prior to the operation, the revolving arm 20 is displaced to the position spaced away from the starting position so that the patient can approach the patient positioning station 40 of the elevation unit 12 without any interference from the revolving arm 20, and the operator can examine the patient for proper positioning at the patient positioning station 40.

Once the revolving arm 20 has moved to the displaced position, the patient is able to approach the patient positioning station 40. If necessary, by operation of the elevating switch for moving the elevation unit 12, a level adjustment of the patient positioning station 40 can be done for the patient. The patient P grips the handles 46 with his chin mounted on the chin rest 42 and with his temporal lobes abutting the restricting members 44. In this condition, the operator OP can look and confirm whether the patient has been properly positioned.

Figure 11:
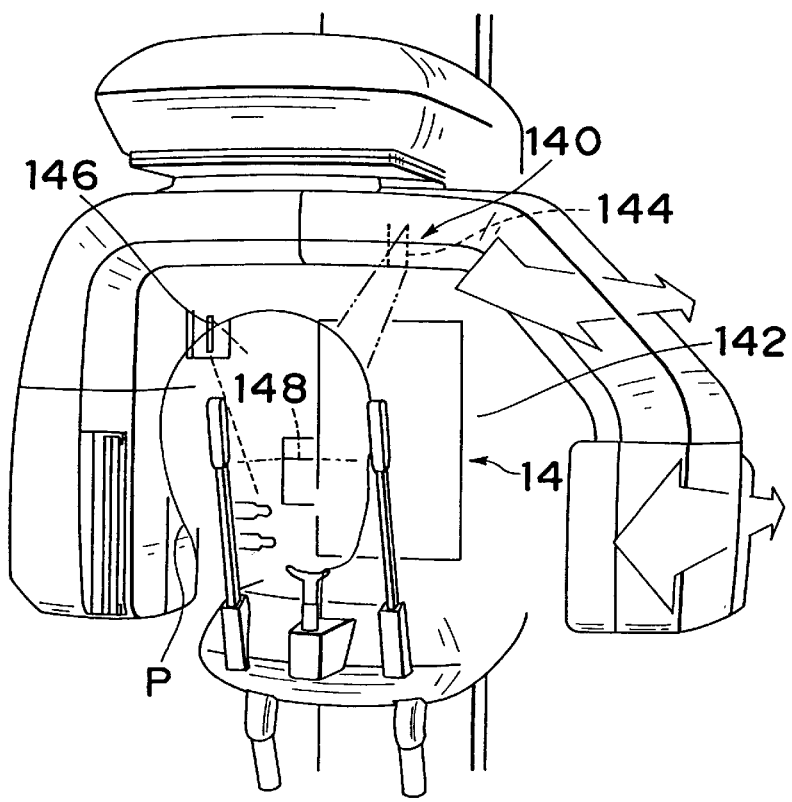
FIG. 11 is a diagram that illustrates an optical positioning device for improving the positioning of the patient with respect to the X-ray apparatus shown in FIG. 1.
Figure 12:
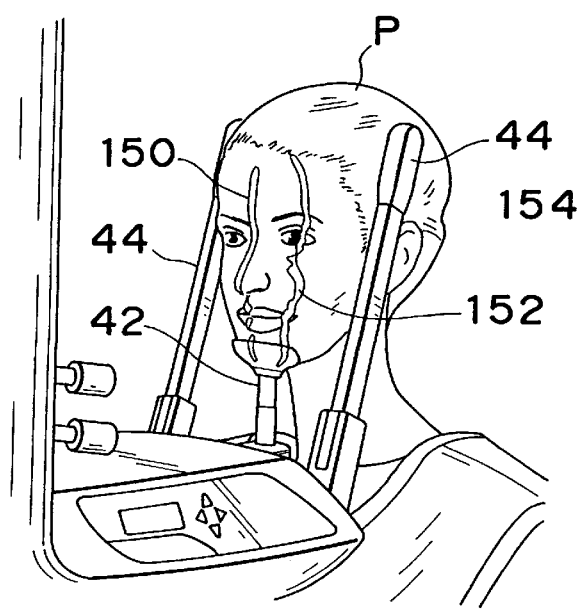
FIG. 12 is a diagram that corresponds to FIG. 11 and illustrates an optical positioning device for improving a positioning of the patient with the X-ray apparatus shown in FIG. 1.

Referring to FIG. 11, for the operator to determine whether the patient is properly positioned, an optical device 140 may be incorporated into the X-ray apparatus 2. The optical device 140 includes a vertical slot 144 and a horizontal slot 148, both formed in the housing 142 which outlines the vertical portion 14 of the elevation unit 12, and another vertical slot 146 formed in the revolving arm 20. Behind the slots 144, 146 and 148, associated lamps (not shown) are positioned for projecting line beams therefrom, respectively. As shown in FIG. 12, if the patient is properly positioned at the positioning station 40, line beams projected from the vertical slots 144 and 146 will substantially correspond to a median line of the patient and a tomogram position, respectively, and another line beam projected from the horizontal slot 148 will substantially correspond to a plane extending through eyes and ears of the patient. Therefore, simply by looking at the patient's face on which the line beams are projected, the operator easily can see whether the patient is properly positioned.

After completion of the patient's positioning, the operator can select a required photographing mode at the input 38. Next, once the switch 123 for emitting the X-ray beam is turned on, a signal or information is transmitted from the memory 126 to the controller 122 according to the selected photographing mode. In response to this, the controller 122 generates signals corresponding to the information and then transmits the same to the respective drive circuits 128, 130, 132, 134, and 136. The drive circuits 128, 130, 132, 134, and 136 each generate digital signals to associated stepper motors 64, 76, 94, 106 and 118, causing the revolving arm 20 to revolve along a path which is suitable for the selected photographing mode.

It should be noted that, if the revolving arm 20 is at the displaced position before its revolving, it is first returned to the starting position of the photographing. Simultaneously with or after the rotation of the revolving arm 20, the X-ray generator 28 generates the X-ray beam which will be projected toward the X-ray receiver 30. The projected X-ray beam transmits through the patient and then to the slot 85, exposing the X-ray receiving surface 37 of the cassette 36.

Specifically, when the standard panoramic tomogram for taking a panoramic picture along the patient's dentition is selected, the pivot motor 94, Y-motor 64 and X-motor 76 are so driven as to satisfy the following conditions:

(a) a ratio of the distance from the X-ray source 32 to a photographic point or target to another distance from the X-ray source 32 to the X-ray receiving surface 37 is substantially constant;

(b) a line connecting the X-ray source 32 and the X-ray receiving surface 37 is substantially perpendicular to the dentition at every incremental photographing portions of the dentition;

(c) a moving velocity of the X-ray source 32 is substantially equal to that of the X-ray receiving surface 37;

(d) moving velocities of the X-ray source 32 and X-ray receiving surface 37 are controlled so that substantially equal amounts of X-ray energy will be projected to every incremental target portion of the dentition; and (e) the photographic point moves from one end to the other end of the dentition.

Figure 13:
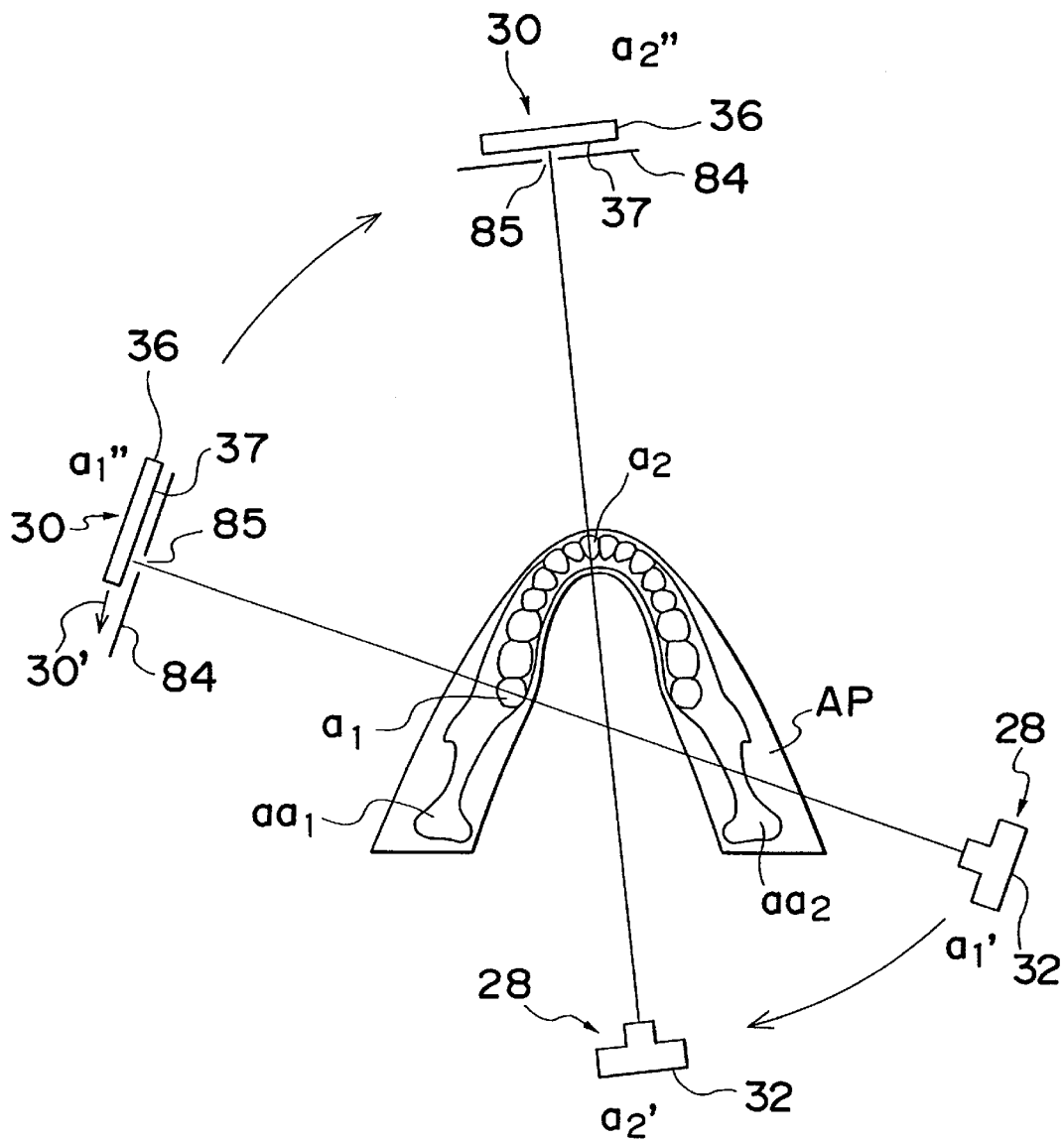
FIG. 13 is a diagram that illustrates a movement of the X-ray generator and X-ray receiver in a panoramic tomography using the X-ray apparatus shown in FIG. 1.

FIG. 13 shows a movement of the X-ray generator 28 and X-ray receiver 30 in the standard panoramic tomogram in which the teeth on a longitudinal sectional line of the dentition AP between mandible portions aa1 and aa2 adjacent opposite ends of a dentition are photographed. However, FIG. 13 shows only a part of the photographing process from a posterior teeth al (right posterior teeth in the drawing) to an anterior tooth a2.

During the operation of the panoramic tomogram, the motor 106 can be turned off so that the X-ray receiving surface 37 is maintained with respect to the X-ray source 32. When film sensitive to the X-rays is employed as the X-ray receiving surface 37, the motor 118 is energized in synchrony with the motors 64 and 76. This causes the cassette to move along the film guide 34 in a direction indicated at 30' in synchronous with the moving velocity of the revolving arm 20.

If the CCD sensor array is employed for the X-ray receiver instead, the cassette is not required to move along the film guide 34. In this instance, however, to reproduce the panoramic photograph of the dentition, the image signal from the CCD sensors should be electrically processed in synchrony with the moving velocity of the X-ray beam along the dentition, i.e., the rotational velocity of the revolving arm.

Specifically, during photographing, the X-ray generator 28 is directed so that at each position the X-ray beam projected form the X-ray source 32 will cross the dentition at an approximately right angle. The X-ray receiver 32, on the other hand, takes positions so that it will face the X-ray generator 28 through the dentition AP for receiving the X-ray beam by the X-ray receiving surface. For example, as shown in FIG. 13, when photographing the anterior tooth al, the X-ray generator 28 takes a position indicated by a1' while the X-ray receiver 30 occupies a position indicated by a1". Then, the X-ray generator 28 moves toward another position a2' while keeping the X-ray beam crossing the dentition at an approximately right angle. The X-ray receiver 30, on the other hand, travels toward the corresponding position a2" while receiving the X-ray beam that has transmitted through the dentition. In this manner, a first half of the dentition is photographed.

Successively, the X-ray generator 28 and X-ray receiver 30 travel with keeping the above-described interrelationship between X-ray generator 28 and X-ray receiver 30 for photographing a second half of the dentition from the anterior tooth a2 to the other posterior tooth aa2. As described above, the standard panoramic tomogram can be obtained.

Figure 14:
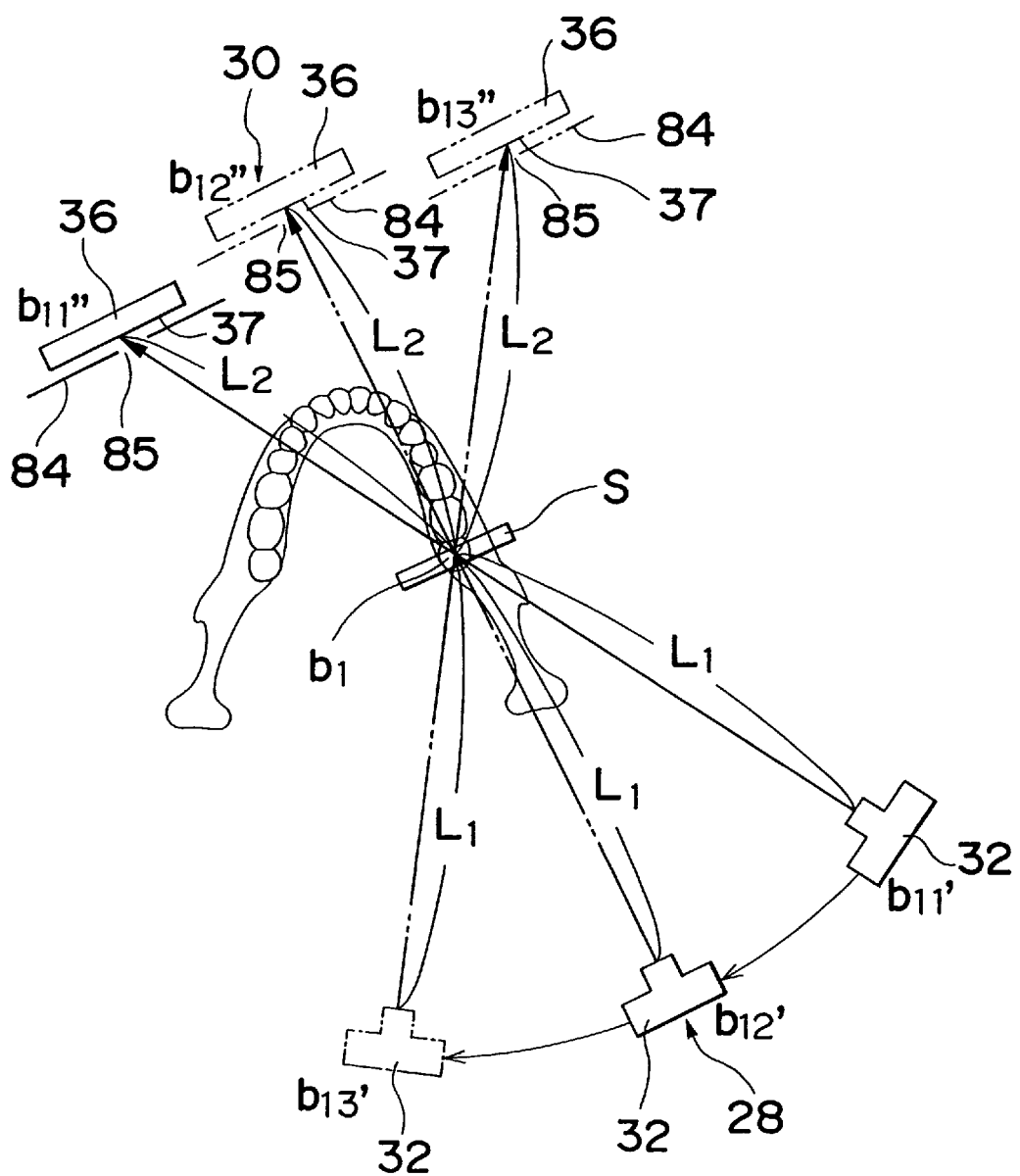
FIG. 14 is a diagram that illustrates a movement of the X-ray generator and X-ray receiver in a linear radiogram using the X-ray apparatus shown in FIG. 1.

FIG. 14 shows a combined movement of X-ray generator 28 and X-ray receiver 30 in the linear tomogram along a transverse sectional plane S of the dentition of the right posterior teeth b1. At the beginning of the photographing, the X-ray generator 28 and X-ray receiver 30 take respective positions b11' and b11" on a line that obliquely crosses the transverse sectional plane S near the posterior tooth b1 so that they face each other through the plane S. In this state, the X-ray receiver 30 receives the X-ray beam transmitted from the X-ray generator 28 through the posterior teeth b1.

Then, in response to the revolving of the arm 20 about the posterior teeth b1 to be photographed, the X-ray generator 28 together with the X-ray source 32 moves through an intermediate position b12' to a final position b13'. Simultaneously, the X-ray receiver 30 moves through an intermediate position b12" to a final position b13". Note that at the intermediate position, the X-ray beam transmitted from the X-ray generator 28 crosses the cross sectional plane S at an approximately right angle. Also, during this movement, the X-ray generator 28 and X-ray receiver 30 take respective positions, so that the X-ray generator 28 faces the X-ray receiver 30 through the posterior teeth b1 being photographed.

In addition, during photographing, X-ray receiver 30 is rotated by the motor 106 in synchrony with the rotation of the revolving arm 20, so that the X-ray receiving surface 37 is kept parallel to the transverse sectional plane S of the posterior teeth b1. Unlike the panoramic tomogram, the cassette 36 stays fixed with respect to the X-ray receiver 30. In this manner, the linear tomogram is obtained.

For the linear tomogram, the following conditions should be satisfied:

(a) the X-ray generator 28 moves past a position where the X-ray beam perpendicularly crosses the position to be photographed on the transverse sectional plane;

(b) the X-ray receiver 30 receives the X-ray beam transmitted from the X-ray generator 28;

(c) the X-ray generator 28 and X-ray receiver 30 rotate about the position to be photographed while they face each other through the position; and (d) the X-ray receiving surface 37 receives a required amount of X-ray enough for photographing.

It has been recognized that the ratio L1:L2 of a distance from the X-ray source 32 to the photographing position to a distance from the X-ray receiving surface 37 to the photographing position should be kept constant.

Although the X-ray generator 28 and X-ray receiver 30 are moved with the revolving arm 20, the present invention is not limited thereto. In this event, however, the generator 28 and receiver 30 should be positionally maintained with respect to each other through the transverse sectional plane. Also, the X-ray receiving surface 37 should be kept parallel to the plane running through the portion to be photographed. Further, the distance ratio L1:L2 should be kept constant. The X-ray generator 28 and/or X-ray receiver 30 may be moved parallel to the plane.

The X-ray device 2 can be designed so that the X-ray receiver 30 is supported by the shaft 102, where the shaft 102 is not connected to any motor. In this instance, the X-ray receiver 30 is rotated by the rotational force transmitted from the motor 106 through the shaft 108 positioned behind the shaft 102, i.e., away from the X-ray generator 28. This allows the wall of housing adjacent the X-ray generator 28 to be spaced further away from the patient. As a result, it is not necessary to open the wall toward the patient, which would otherwise be required by a conventional X-ray device in which the motor is directly connected with a shaft that supports an X-ray receiver. Further, the patient positioned between the X-ray generator 28 and receiver 30 will be comparatively less confined.

Figure 15:
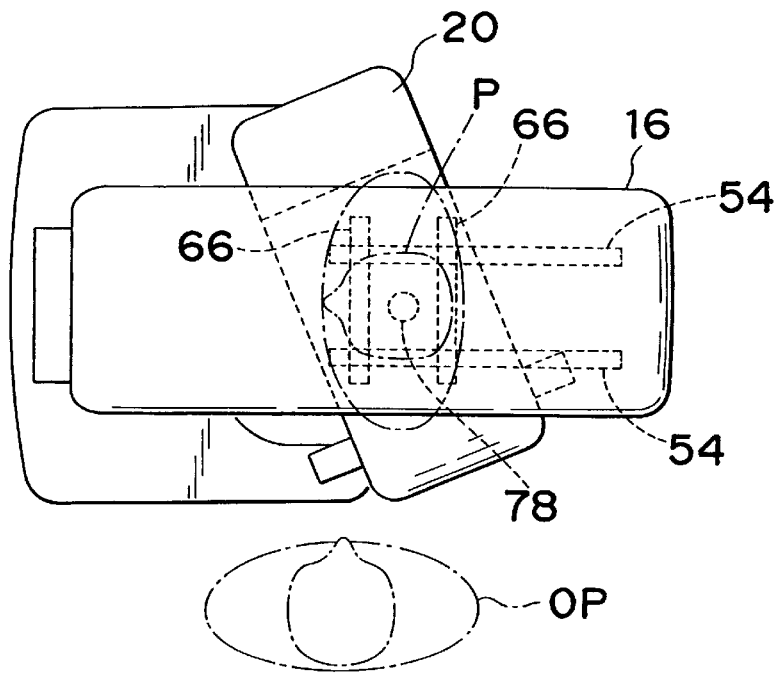
FIG. 15 is a plan view of the X-ray apparatus shown in FIG. 1 in which the revolving arm is located at a position from which the photographing can be started.

When displacing the revolving arm, it is necessary to prevent the revolving arm from making a collision with the patient approaching the patient positioning station. FIG. 15 shows an initial position of the revolving arm 20, which will be referred to as reference position hereinafter as necessary. In this reference position, the shaft 78 of the transport mechanism 52 is almost above the head of the patient P. However, the revolving arm 20 may prevent the operator OP from looking sideways at the side view of the patient. Under these circumstances, the operator can have a difficulty in seeing whether the patient is properly positioned in the patient positioning station 40.

Figure 16:
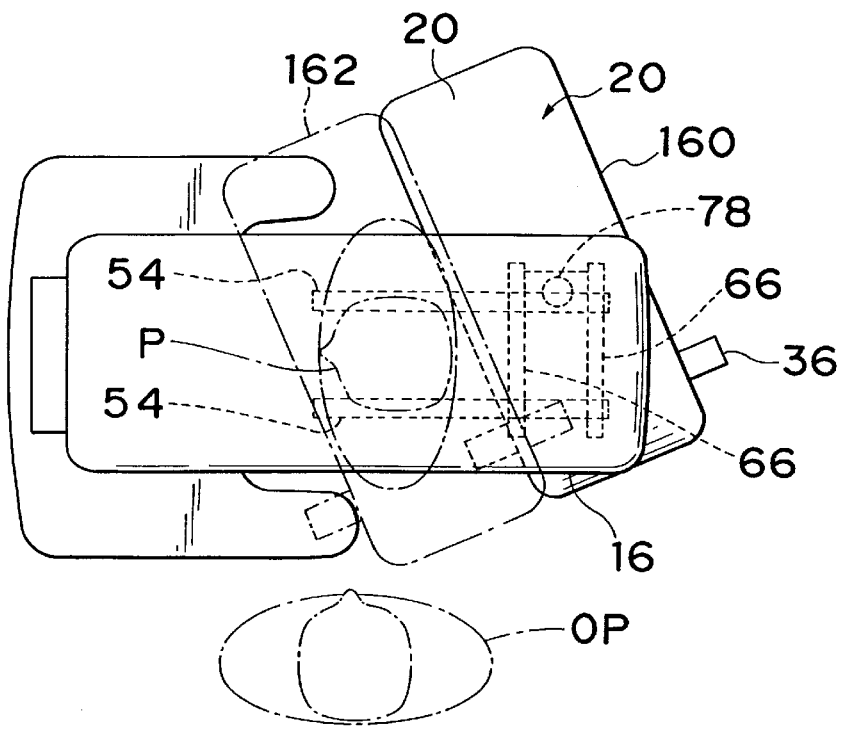
FIG. 16 is a plan view of the X-ray apparatus shown in FIG. 1, showing a position (displaced position) of the revolving arm at the time of patient positioning.
Figure 17:
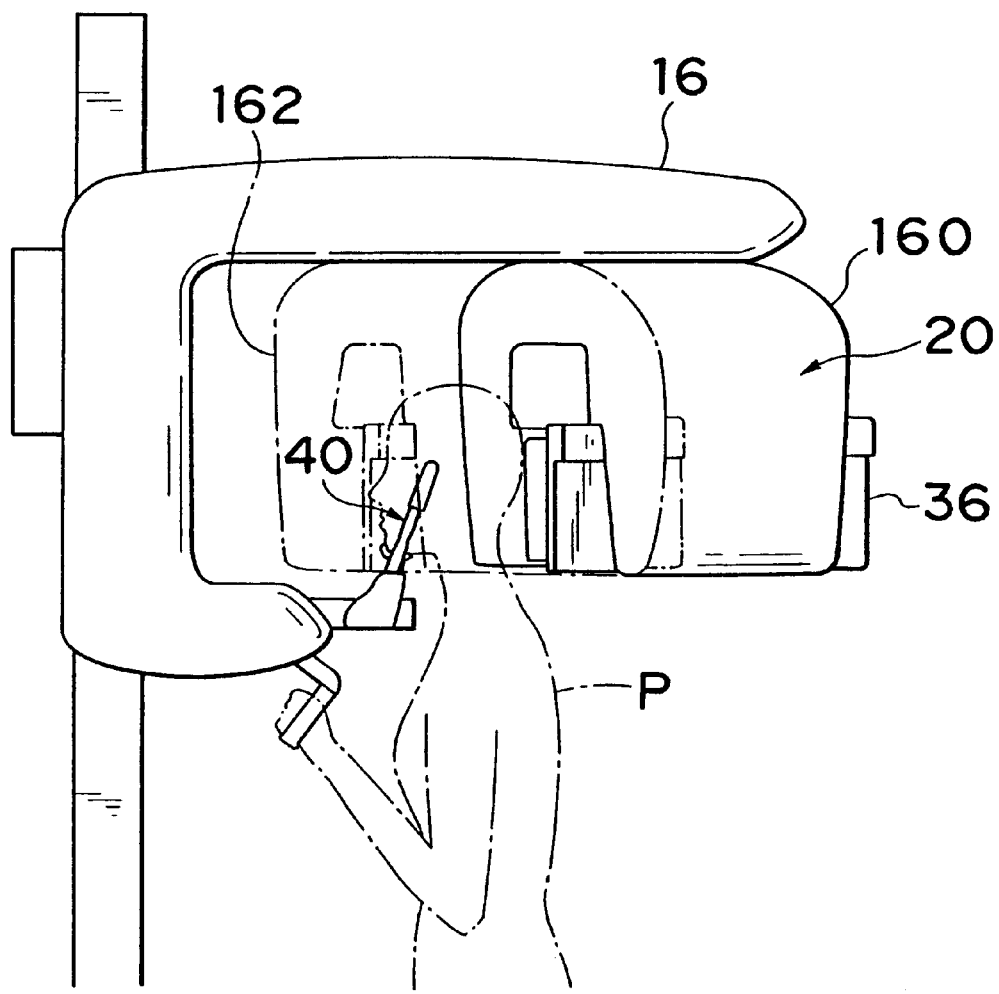
FIG. 17 is a side view of the X-ray apparatus shown in FIG. 1, which corresponds with FIG. 16 to illustrate a position (displaced position) of the revolving arm at the time of patient positioning.

To counter this, as shown in FIGS. 16 and 17, the X-ray device of the preferred embodiment includes the switch 125 in the input 38. Also, the memory 126 stores a program capable of cooperating with the switch 125. With this arrangement, once the switch 125 is turned on, the controller 122 calls the program from the memory 126 to energize the Y-motor 64 and X-motor 76 and, if necessary, an additional motor 94. This displaces the revolving arm 20 toward a remote position 160 where an area located between the X-ray generator 28 and receiver 30 is out of the head zone of the patient to be positioned at the patient positioning station 40. In this situation, because the X-ray receiver 30 is removed from the space between the operator OP and patient P, the operator OP can easily look at the front and side views of the patient who would be subsequently positioned in the patient positioning station 40.

After the completion of patient positioning operation, once the X-ray projection switch 123 (see FIG. 10) is turned on by the operator OP, Y-motor 64 and X-motor 76 of the transport mechanism 52 and, if necessary, additional motor 94 are energized. Due to this, the revolving arm 20 moves back to the reference position (see FIG. 15) from which the revolving arm 20 (and X-ray receiver 30 and cassette, if necessary) moves to start the selected tomography mode.

Figure 18:
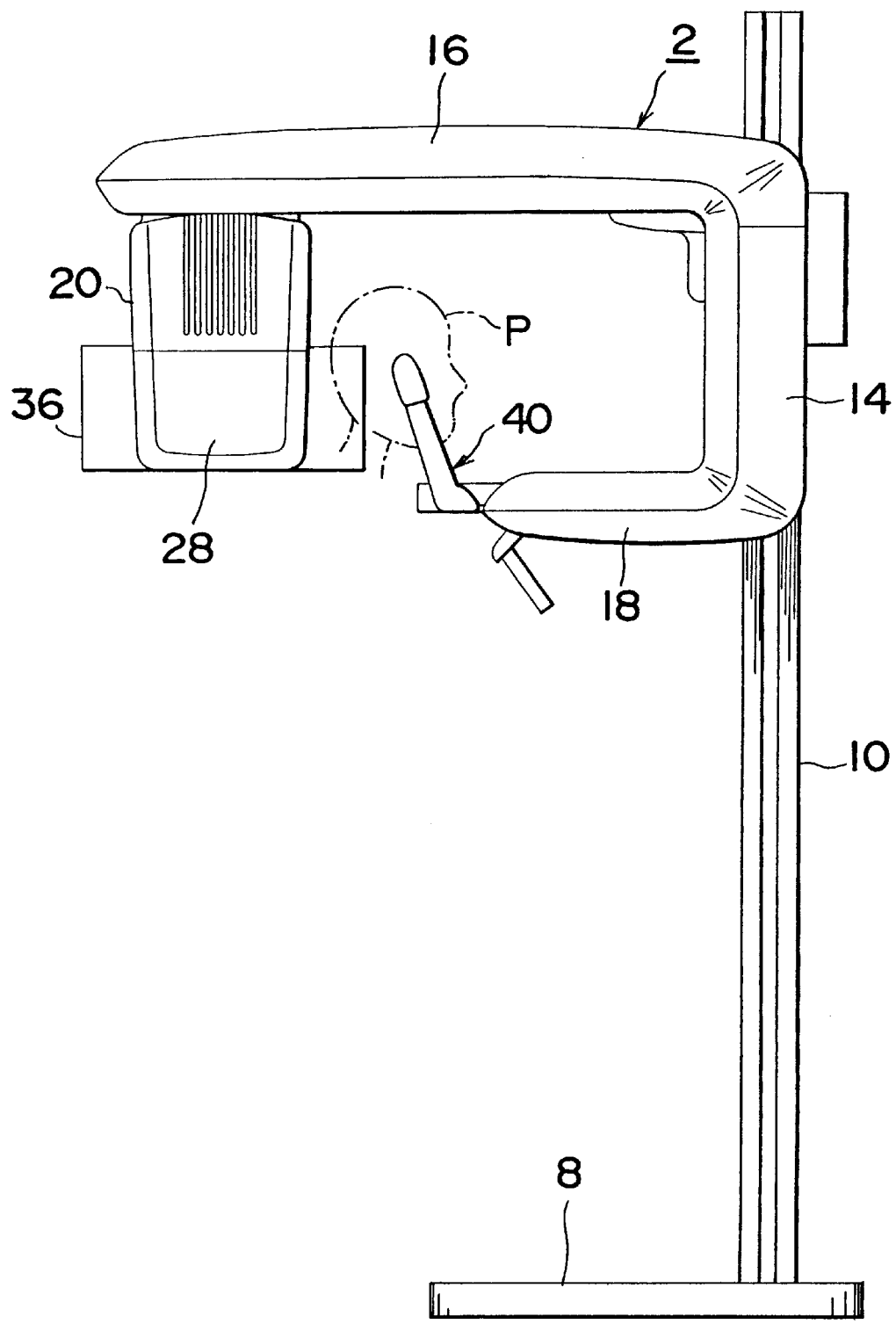
FIG. 18 is a side view of the X-ray apparatus shown in FIG. 1 at the time of patient positioning with the upper portion of the elevation unit being extended in a Y-direction, in which the revolving arm is located behind the patient.

To allow the operator OP to look at the patient's side view, as shown in FIG. 18, the revolving arm 20 may be temporally displaced to a position where the X-ray generator 28 and receiver 30 can oppose each other in the X-direction behind the patient. For this purpose, the upper portion 16 of the elevation unit 12 may be extended rearward of the patient to the extent that a clear space is formed between the patient and the revolving arm 20, as necessary.

Figure 19:
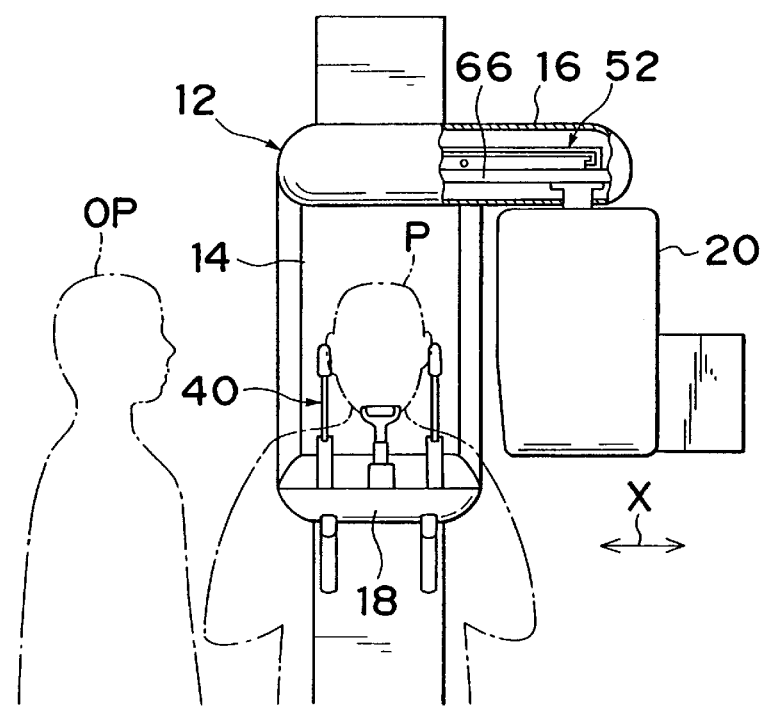
FIG. 19 is a front view of the X-ray apparatus shown in FIG. 1 at the time of patient positioning with the upper portion of the elevation unit being extended in a X-direction, in which the revolving arm is located beside the patient.
Figure 20:
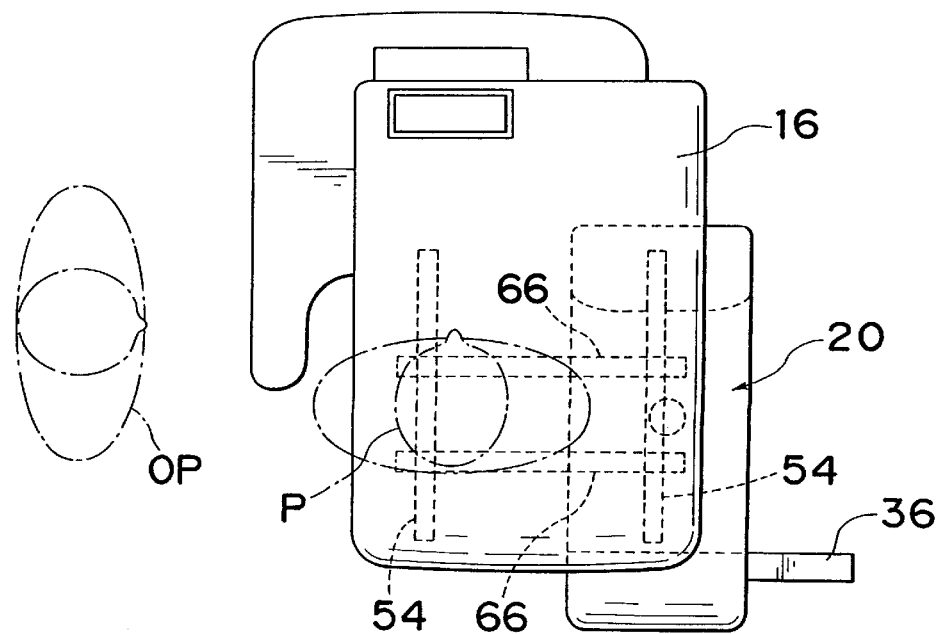
FIG. 20 is a plan view of the X-ray apparatus shown in FIG. 1 at patient positioning with the upper portion of the elevation unit being extended in a X-direction, in which the revolving arm is located beside the patient.

In this modification the revolving arm 20 is displaced behind the patient P, though, it may be displaced to alternative positions. For example, as shown in FIGS. 19 and 20, the revolving arm 20 may be displaced to the lateral side of the patient. This also permits the operator to look at the patient's side view and then determine whether the patient has been properly positioned.

Also, not only to allow the operator to position the patient but also to permit the patient to approach the positioning station more easily, the upper portion 16 of the elevation unit 12 may be enlarged with respect to the X-direction to allow the X-rails 66 installed therein to be extended in the same direction, thereby allowing the revolving arm 20 to be removed from the patient's approach. This provides the patient with direct access to the positioning station without any interference from the revolving arm.

In addition, the cassette 36 in the displaced revolving arm 20 may also be moved to a position farthest from the patient's approach. This further improves the patient's access to the positioning station. In this instance, extending one side, not both sides, of the upper portion 16 would be sufficient, as illustrated.

Figure 21:
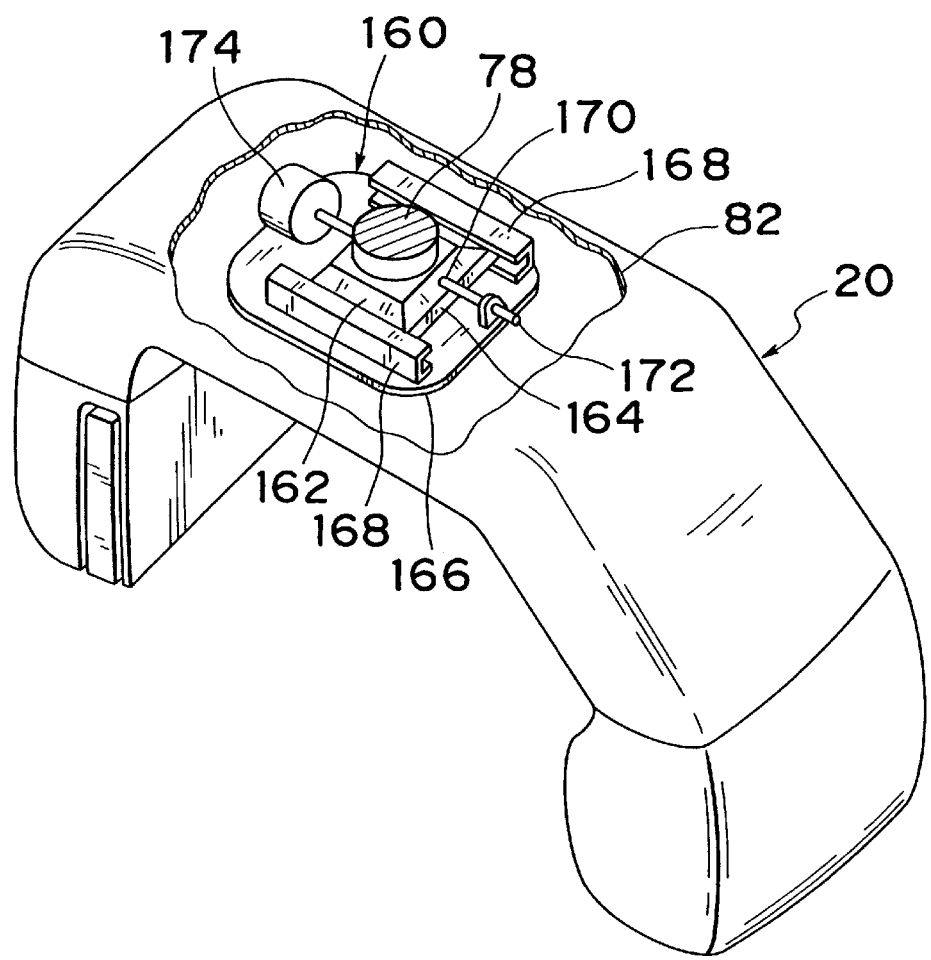
FIG. 21 is a perspective view, partially in section, of the revolving arm shown in FIG. 1, showing a second transport mechanism incorporated in the housing.
Figure 22:
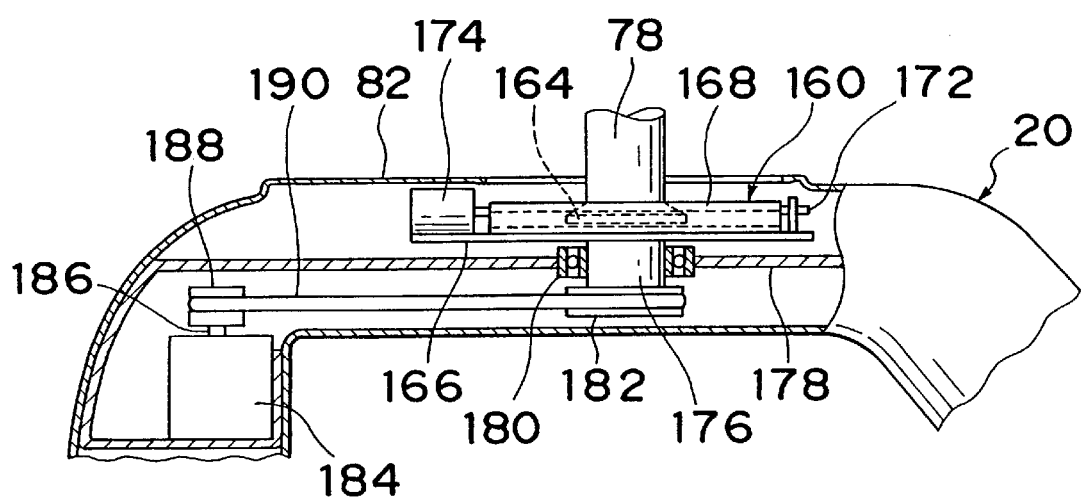
FIG. 22 is a transverse sectional view of the second transport mechanism incorporated in the housing of the revolving arm shown in FIG. 21.

To increase the displacing distance without enlarging the volume of the elevation unit 12, as shown in FIGS. 21 and 22, a second displacing mechanism generally indicated by reference numeral 160 may be provided in the housing 82 of the revolving arm 20. The second displacing mechanism 160 includes a connector 162 fixed at a lower end portion of the revolving shaft 78. The connector 162 has a member 162 in the form of rectangle, a pair of opposing side-edges of the rectangular member 162 being guided by a corresponding pair of rails 168 secured on a base plate 166 so that the rectangular member 162 can reciprocally move along the rails 168 relative the base plate 166. Also, the connector 162 has a threaded hole 170 extending parallel to the rails 168, in which threaded hole 170 a lead screw 172 is engaged. The lead screw 172 is connected by a drive at one end thereof with a motor (stepper motor) 174 secured on the base plate 166, allowing the base plate 166 to move horizontally relative to the revolving shaft 78 by driving the motor 174.

As shown in FIG. 22, a vertical shaft 176 extending parallel to the revolving shaft 78 is secured at an upper end thereof to a lower surface of the base plate 166. The shaft 176 is supported by a bearing 180 fixedly mounted on a frame 178 which is secured on the housing 82 of the revolving arm 20. Also, a lower end of the shaft 176 integrally carries a pulley 182. Further, a motor 184 is fixedly mounted in the housing 82 having an output shaft 186 which carries another pulley 188. An endless belt 190 is entrained about the pulleys 182 and 188.

With the second displacing mechanism 160, not only when the X-ray device is in the photographing state (including the rotating state) but also when it is in the displaced position, the shaft 176 stays in a coaxial configuration with respect to the revolving shaft 78. In operation, a rotation of the output shaft 186 of the motor 184 is serially transmitted through the pulley 188, endless belt 190, pulley 182 and shaft 176 to the base plate 178 fixed to the shaft 176. The rotation of the base plate 178 is in turn transmitted through the connector 162 to the revolving shaft 78, causing the revolving arm 20 to rotate relative to the elevation unit 12.

When the revolving arm 20 is in the displaced position, the revolving arm 20 is preferably oriented so that the patient can approach the positioning station and/or the operator can view the patient to be positioned in the positioning station. For this purpose, the motor 184 is driven to turn the revolving arm 20 into a suitable direction and also the motor 174 is energized to move the revolving shaft 78 relative to the base plate 178, i.e., move the revolving arm 20 relative to the elevation unit 12.

It is of course possible to displace the revolving arm 20 to any desirable position depending upon the purpose by moving the revolving shaft 78 and also using the first displacing mechanism 52 mounted in the upper portion 16 in cooperation with the second displacing mechanism 160 as necessary.

In view of above, by using the second displacing mechanism 160 as well as the first displacing mechanism 52, the revolving arm 20 can further be displaced, facilitating the patient's approach toward the positioning station and/or operator's viewing of the patient positioned at the station.

Although the second displacing mechanism 160 is installed in the housing 84 of the revolving arm 20, it may be arranged in the upper housing 50 of the elevation unit 12 or between the housings 50 and 84.

Also, the second displacing mechanism 160 is not limited to the above described. An alternative mechanism such as disclosed in Japanese Patent Application (Japanese Patent Laid-Open Publication No. 7-13615) can be employed instead.

Figure 23:
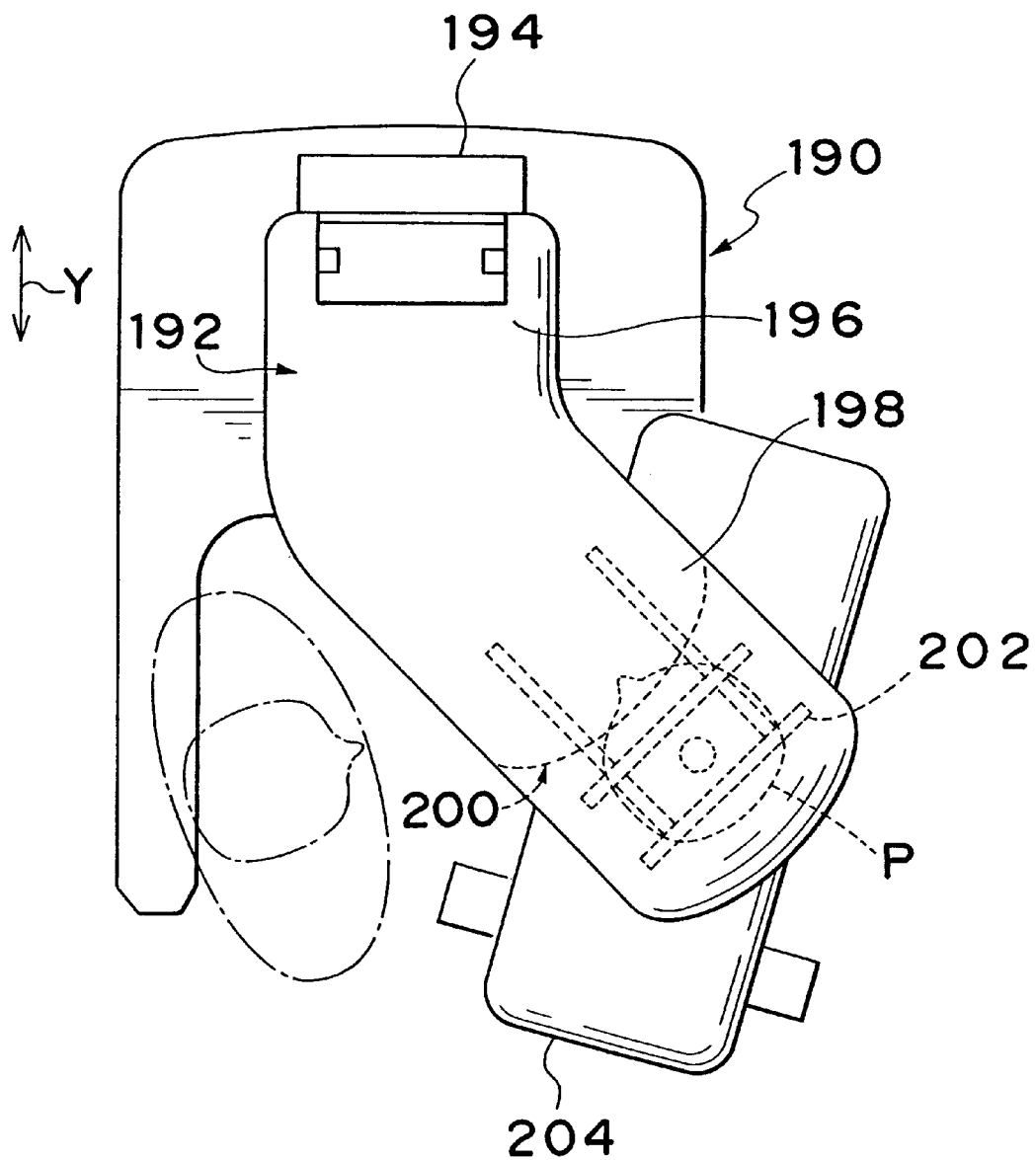
FIG. 23 is a plan view of a second embodiment of an X-ray apparatus according to the present invention in which the upper and lower portions of the elevation unit are angled at mid portions thereof at about 45 degrees with respect to the Y-direction.

FIG. 23 shows a second embodiment of a dental X-ray apparatus of the present invention, generally indicated by reference numeral 190. In this X-ray apparatus, an upper portion 192 of an elevation unit integrally includes a first upper portion 196 extending from a column 194 in the Y-direction and a second upper portion 198 extended from an distal end of the first upper portion 196 and angled therewith about 30 to 60 degrees, preferably about 45 degrees. Likewise, a lower portion 200 of the elevation unit may be angled as necessary.

With this arrangement, as illustrated, the patient can be oriented toward that angled direction, allowing the operator OP to look at the patient more easily.

Also in this embodiment, the use of the displacing mechanism 202 of the upper portion 192 of elevation unit and, if necessary, the second displacing mechanism of the revolving arm 20 will ease the patient's approach to the positioning station and/or the operator's view of the patient.

Figure 24:
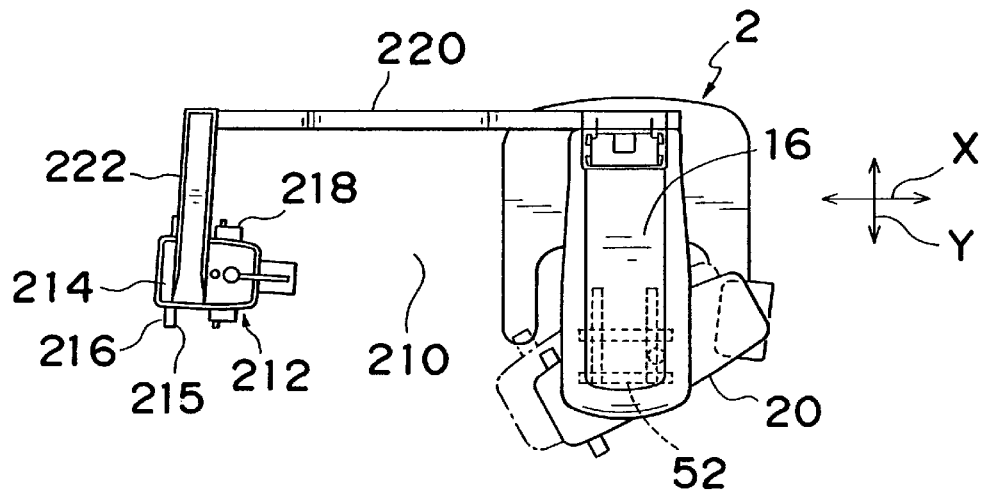
FIG. 24 is a plan view of a third embodiment of an X-ray apparatus according to the present invention with a cephalostat on the left-hand side, where a position of the revolving arm for a cephalogram is indicated by a solid line while a position of the revolving arm for other photographing is indicated by a phantom line.
Figure 25:
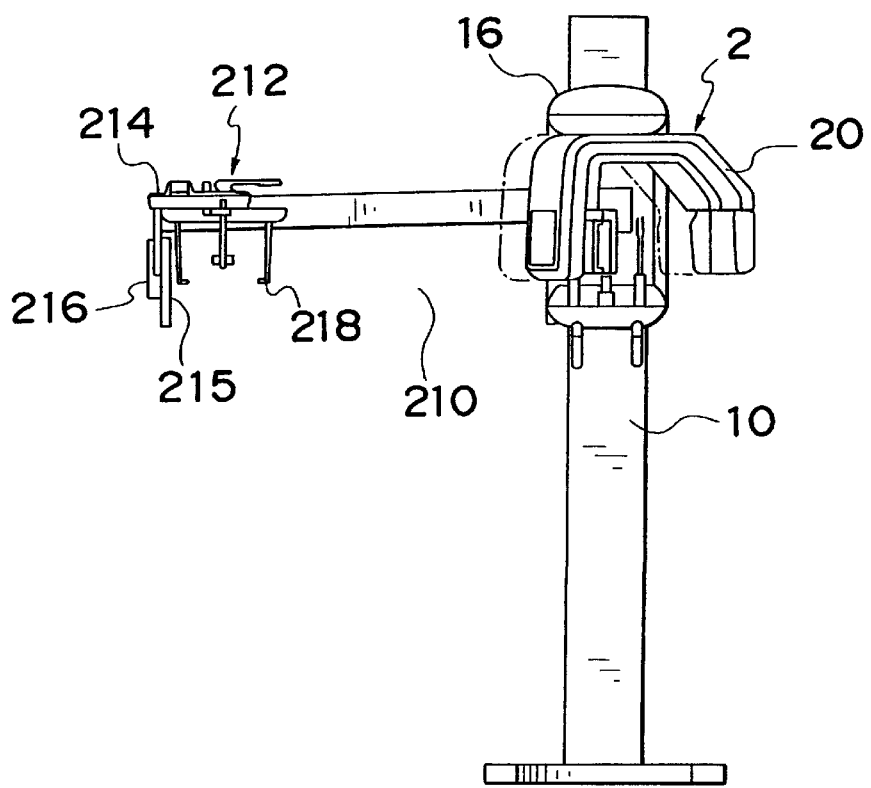
FIG. 25 is a front view of the X-ray apparatus with the cephalostat shown in FIG. 24.

FIGS. 24 and 25 illustrate a third embodiment of an X-ray apparatus according to the present invention additionally having a cephalostat generally indicated by reference numeral 212. The X-ray apparatus, except for the cephalostat, may have the same construction as that described above. The cephalostat 212 has a frame 214 including a cassette holder 216 for holding a cassette 215 and a positioning device 218 for holding and positioning the head of patient. The cassette 215 may include a X-ray receiving film or X-ray fluorescent sheet, or a MOS sensor. Further, the cephalostat 212 includes an X-revolving arm 220 which horizontally extends in the X-direction from a rear portion of the elevation unit 12 of the X-ray device 210 and a Y-revolving arm 222 which extends from a distal end of the X-revolving arm 220 in the Y-direction. In addition, the frame 214 is supported at the distal end of the Y-revolving arm 222. In the cephalogram using the X-ray device 210 equipped with the cephalostat 212, the revolving arm 20 is displaced to a position (shown by a solid line) farthest from the cassette holder 216 with respect to the X-direction with the aid of the X/Y-transport mechanism 52 of the X-ray device 210 so that the cassette spaces a predetermined distance of 180 centimeters away from the X-ray generator. Simply by moving the revolving arm 20, the area occupied by the X-ray device with the cephalostat can be minimized with respect to the X-direction.

Figure 26:
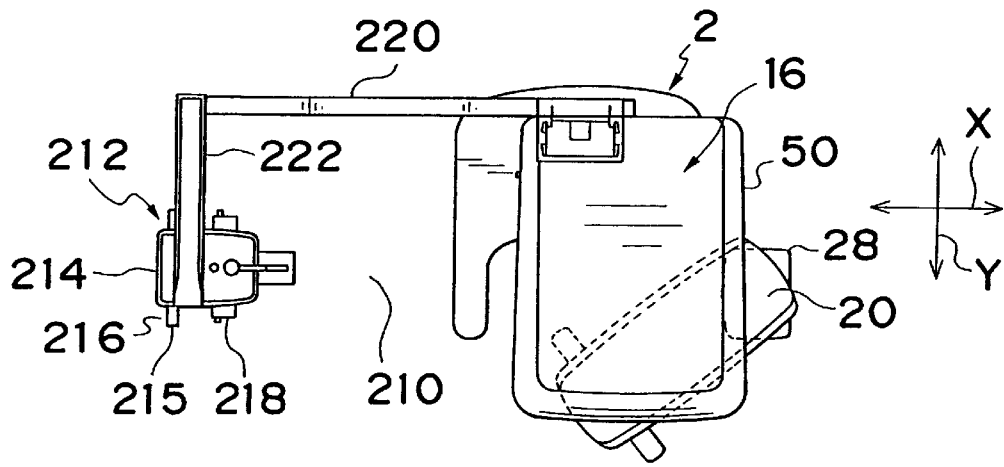
FIG. 26 is a plan view of the X-ray apparatus with a cephalostat shown in FIG. 24, in which the upper portion of the elevation unit is extended in the X-direction.
Figure 27:
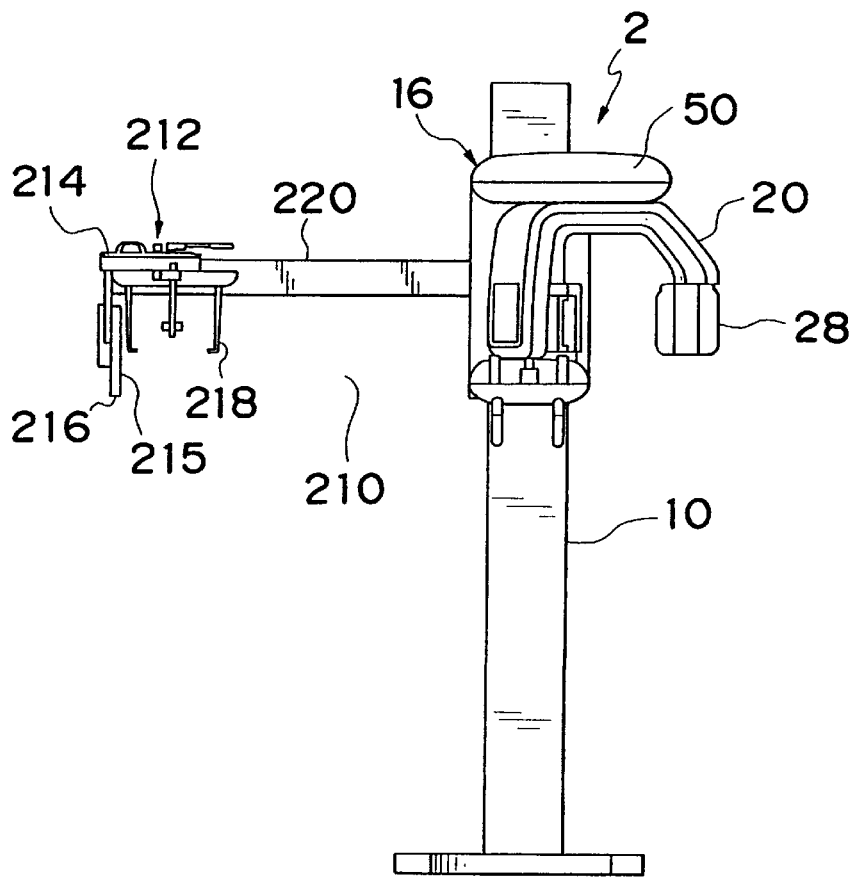
FIG. 27 is a front view of the X-ray apparatus with the cephalostat shown in FIG. 26.

As shown in FIGS. 26 and 27, the housing 50 of the upper portion of the elevation unit in the X-ray device with the cephalostat may be extended in the direction away from the cephalostat, and the X-rails of the X/Y-transport mechanism in the housing 50 may also be extended in the same direction. In this instance, both a length of the X-revolving arm and a distance between the X-ray device and the cephalostat can further be minimized.

Figure 28:
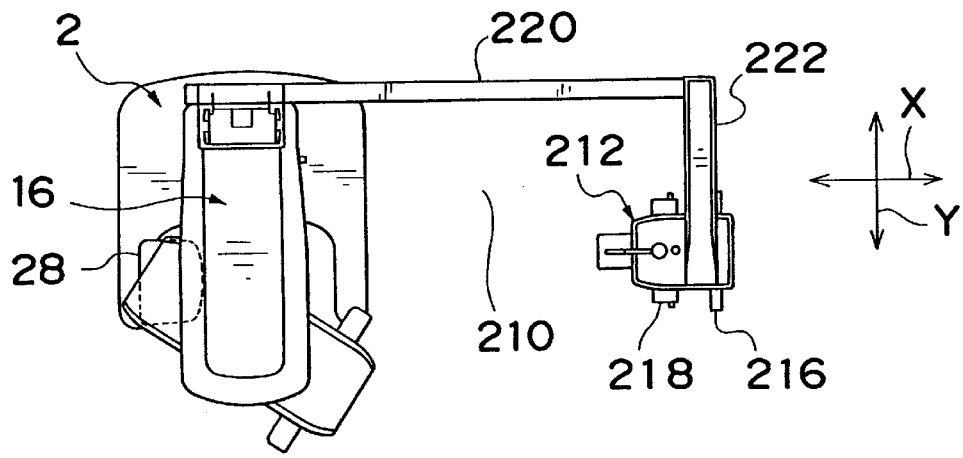
FIG. 28 is a plan view of a fourth embodiment of an X-ray apparatus according to the present invention with the cephalostat on the right-hand side.
Figure 29:
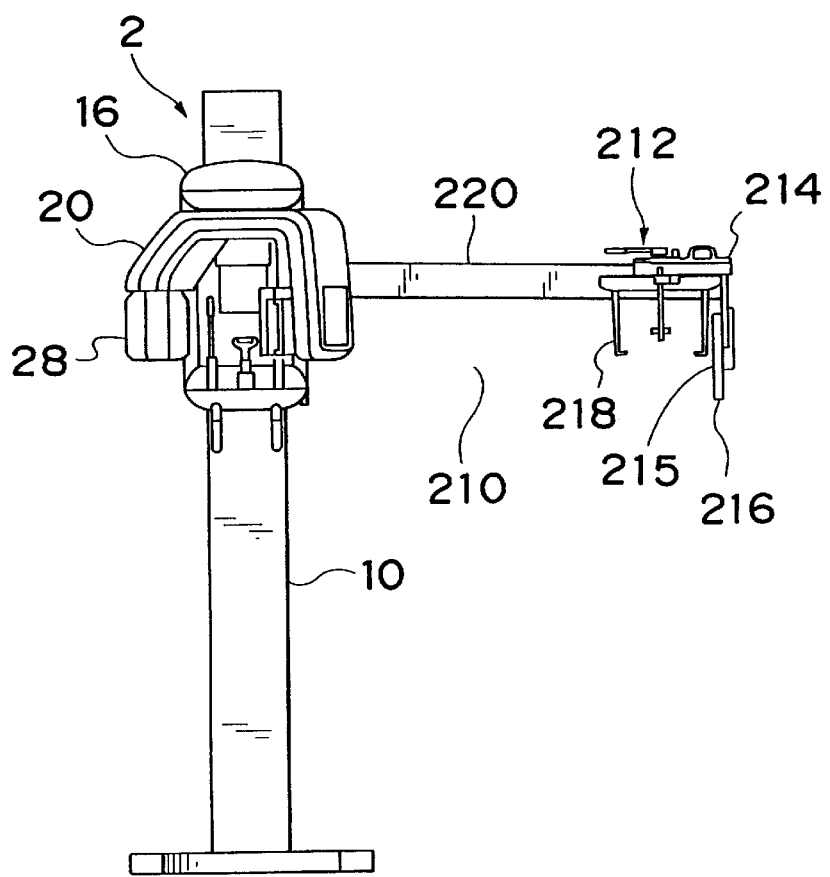
FIG. 29 is a front view of the X-ray apparatus with the cephalostat shown in FIG. 28.

Although in the embodiment shown in FIGS. 24 and 25, and 26 and 27 the cephalostat is arranged on one side, i.e., the left-hand side, of the X-ray apparatus, it may be positioned on the opposite side i.e., the right-hand side, instead. This configuration is shown in FIGS. 28 and 29, which illustrate a fourth embodiment of an X-ray apparatus according to the present invention.

Figure 30:
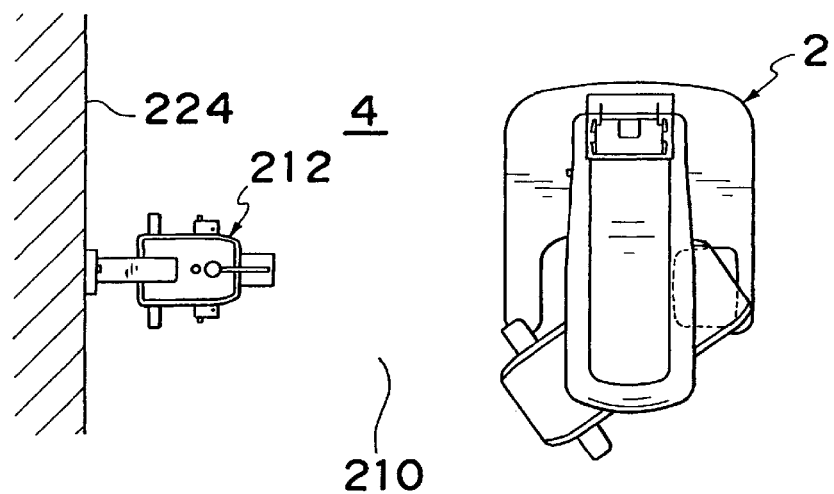
FIG. 30 is a front view of a fifth embodiment of an X-ray apparatus according to the present invention with the cephalostat fixed on a wall.
Figure 31:
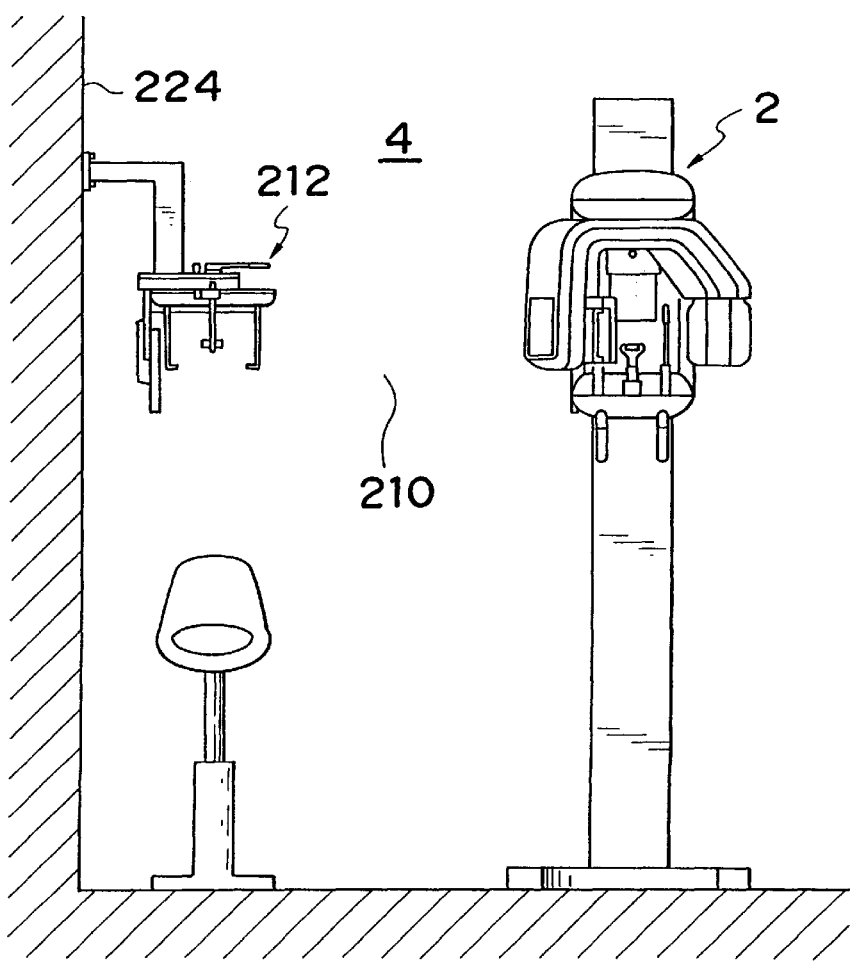
FIG. 31 is a front view of the X-ray apparatus shown in FIG. 30.

FIGS. 30 and 31 show a fifth embodiment of an X-ray apparatus according to the present invention, in which the cephalostat 212 is disconnected from the X-ray device 10 and the frame 214 is fixed on a wall 224 of the X-ray chamber 4. With this arrangement, in the cephalogram, the revolving arm can be displaced to a position farthest from the cephalomat using the X/Y-transport mechanism of the X-ray apparatus. This arrangement minimizes the overall area occupied by the X-ray apparatus including the cephalostat when not in cephalogram operation.

Figure 32:
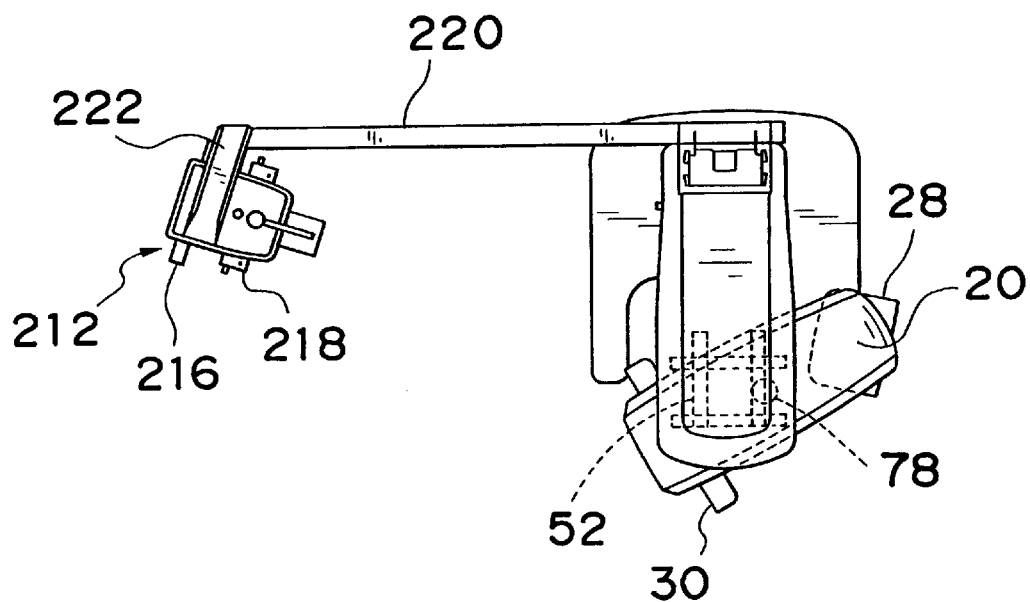
FIG. 32 is a plan view of a sixth embodiment of an X-ray apparatus according to the present invention in which an X-ray film is oriented in a direction angled with the X-direction.

Additional reduction in the space required for the X-ray apparatus can be obtained by means of the X-ray transport mechanism 52, for example, in FIG. 24. Although the space required by the X-ray apparatus of FIG. 24 with the celphalostat with respect to the X-direction at the cephalogram is minimized by moving the revolving arm 20 to the farthest position from the cephalostat, as shown in FIG. 32, it may also be reduced by moving the revolving arm 20 to a farthest position from the column using the X/Y-transport mechanism 52. In this arrangement, as shown in FIG. 32, the Y-revolving arm 222 supporting the frame 214 may be oriented to define a horizontal angle of more than 90 degrees with respect to the X-revolving arm 220 so that the cephalostat 212 faces the X-ray generator 28.

If necessary, in order to move the X-ray receiver 30 out of the area between the X-ray generator 28 of the X-ray apparatus and the X-ray receiving surface or film of the cephalostat 212, the housing 84 of the X-ray receiver 30 may be turned relative to the main housing 82 of the revolving arm 20 by driving the motor and thereby rotating the shaft which connects the housing 84 to the housing 82. This positions the X-ray receiver 30 outside an X-ray beam path.

To direct the X-ray generator 28 toward the X-ray receiving surface of the cephalostat 212, the housing 86 of the X-ray generator 28 may be connected with the housing 82 of the revolving arm 20 by a shaft which is arranged parallel to the revolving shaft 78 and connected by a drive with the motor 87, so that upon driving of the motor 87 the X-ray generator 28 can be rotated relative to the revolving arm housing 82 (see FIGS. 8, 24 and 31).

Figure 33:
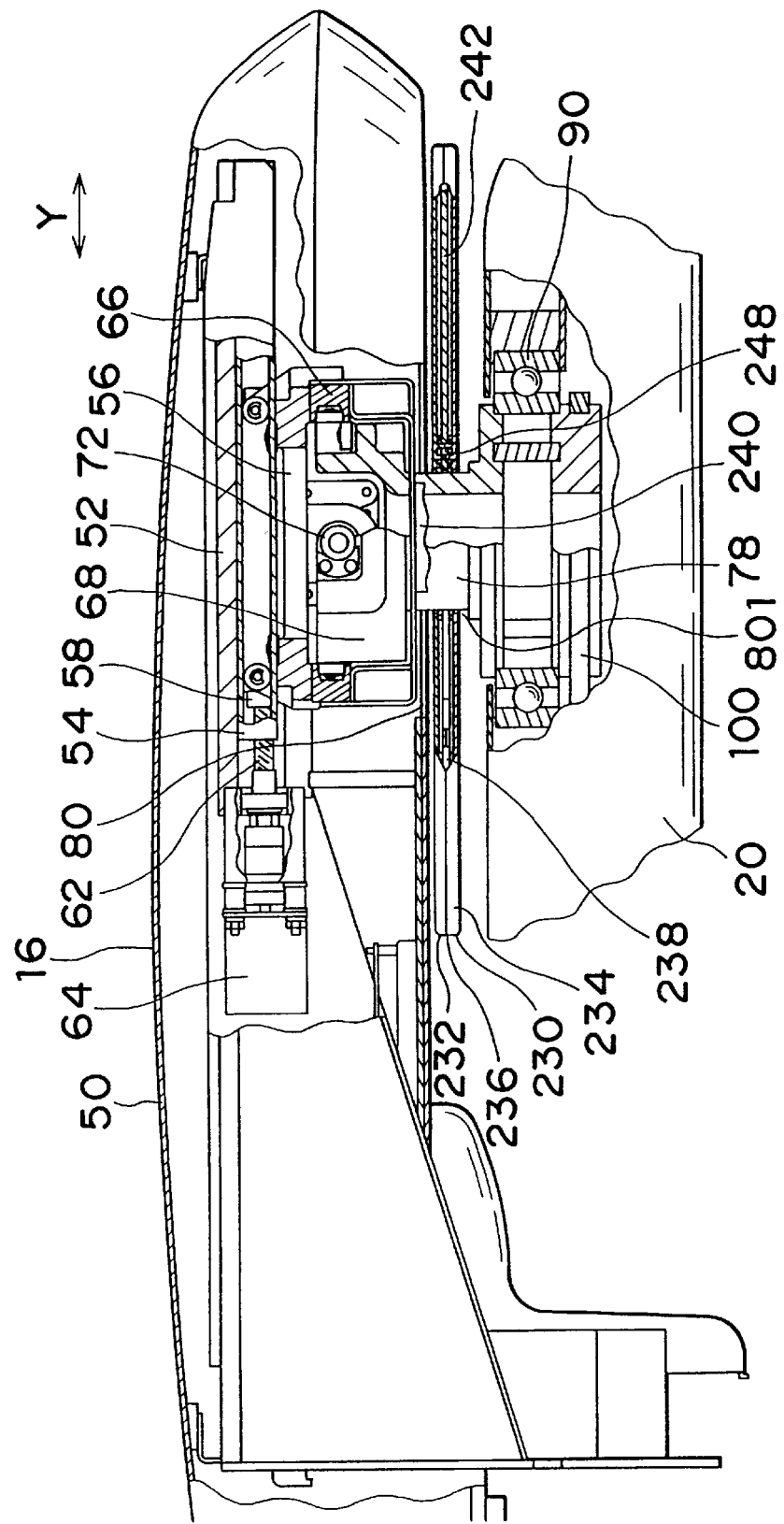
FIG. 33 is a partial cross-sectional side view of an alternative embodiment of the upper portion of the elevating unit that includes a blind mechanism.
Figure 34:
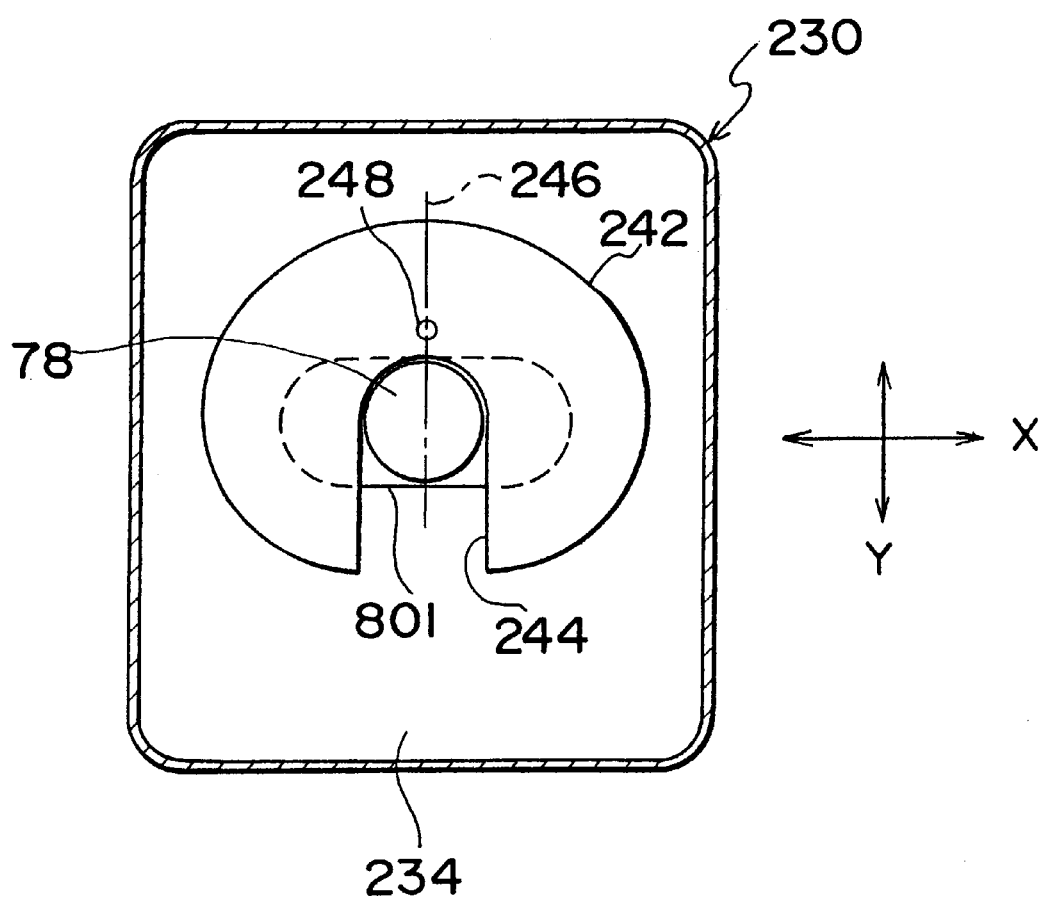
FIG. 34 is a cross-sectional view of a first embodiment of a blind in the blind mechanism of FIG. 33 taken along a line XXXIV—XXXIV in FIG. 33.

A blind can be incorporated into the X-ray apparatus so as to prevent the patient from visually or physically interacting with selected components. Analogously to FIG. 7, FIG. 33, illustrates an alternative embodiment of the elevating unit that includes a blind mechanism. FIGS. 33 and 34 shows a blind unit generally indicated by reference numeral 230 which prevents the patient from viewing or physically interacting with any mechanical structure contained in the upper portion 16 through the opening 80 formed therein. The blind unit 230 includes an upper cover plate 232 and a lower cover plate 234 having the same size and shape. The upper and lower cover plates 232 and 234 are continuously connected at peripheral edges thereof with a connecting portion 236 to from a chamber 238 therebetween. In this embodiment, although the connecting portion 236 is integrally formed with the upper and lower cover plates 232 and 234, it may be an independent member.

The upper cover plate 232 is supported by vertical revolving arms 240 connected with the Y-table 56 and extended down through the opening 80 of the housing 50 so that the blind unit 230 will be transported with Y-table 56 in the Y-direction. To allow the revolving shaft 78 to move in the X-direction relative to the upper and lower cover plates 232 and 234, the upper and lower plates 232 and 234 are formed with an elongated opening 801 extending in the X-direction.

A blind 242, which is mounted in the chamber 238, is made from a doughnut-like plate and formed with a cutout or slot 244 extending from an outer periphery to an inner periphery. As shown in FIG. 34, the blind 242 is mounted for rotation about an axis 248 which is located on an imaginary line 246 running across the center of the opening 80.

With this blind unit 230, when the revolving shaft 78 is moved in the X-direction, it comes into contact with an inner edge of the slot 244. This causes the blind 242 to rotate about the axis 248, covering the substantial portion of the opening 801, not occupied by the shaft 78. Due to this, the mechanical structure in the housing 50 is substantially obscured from the patient's view.

It should be noted that the axis 248 may be a pair of bosses each projected to each other from inner surfaces of the upper and lower cover plates 232 and 234, respectively, or a pin supported by the plates 232 and 234. Instead, the axis 248 may be a portion of the upper or lower cover plate formed integrally therewith.

Figure 35:
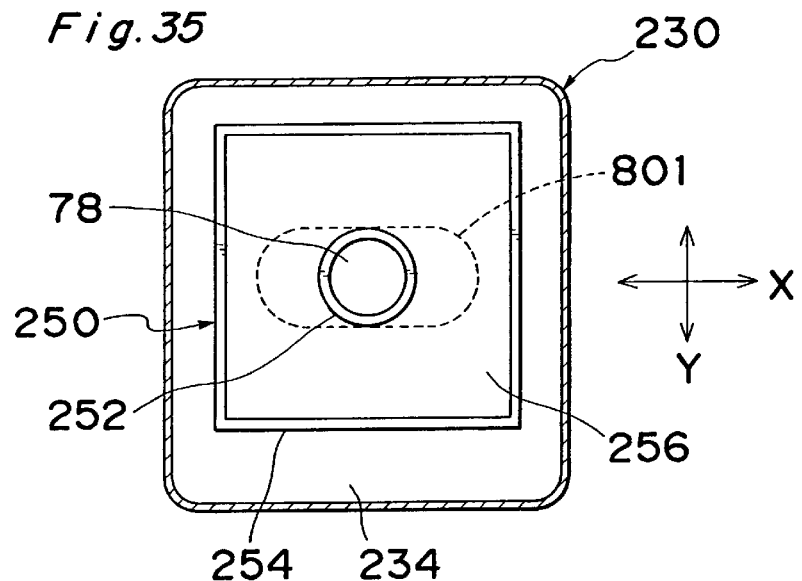
FIG. 35 is a plan view of a second embodiment of a blind.
Figure 36:
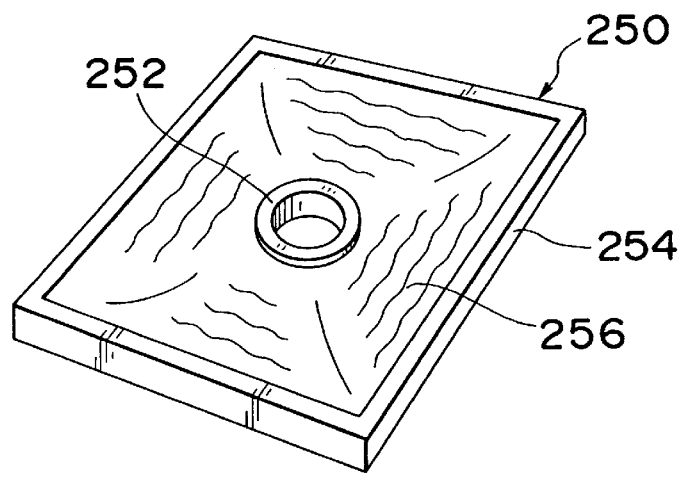
FIG. 36 is a perspective view of the blind shown in FIG. 35.
Figure 37:
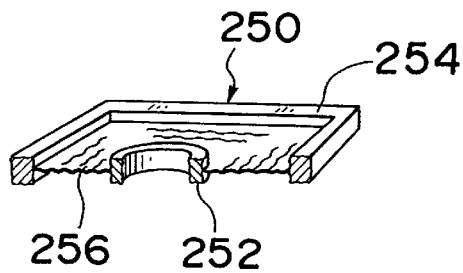
FIG. 37 is a perspective view in section of the blind shown in FIG. 35.

The blind may be formed in different ways without departing from the scope of the present invention. FIGS. 35 to 37 show additional embodiments of the blind generally indicated by reference numeral 250. The blind 250 includes a ring 252 which has an inner diameter slightly larger than the outer diameter of the shaft 78 and is mounted about the shaft 78, a frame 254 fixed on the cover plate 232 or 234, and an expandable flexible sheet 256 made from thin rubber sheet which connects and covers between the ring 252 and the frame 234.

With this blind 250, once the ring 252 is moved with the movement of the shaft 78, the flexible sheet 256 expands with covering the opening 801.

Although the upper cover plate 232 is connected with the Y-table 56, it may be supported on the housing 50 instead. In this instance, as the flexible sheet 256 is made of expandable material such as rubber, the opening is properly covered thereby.

Figure 38:
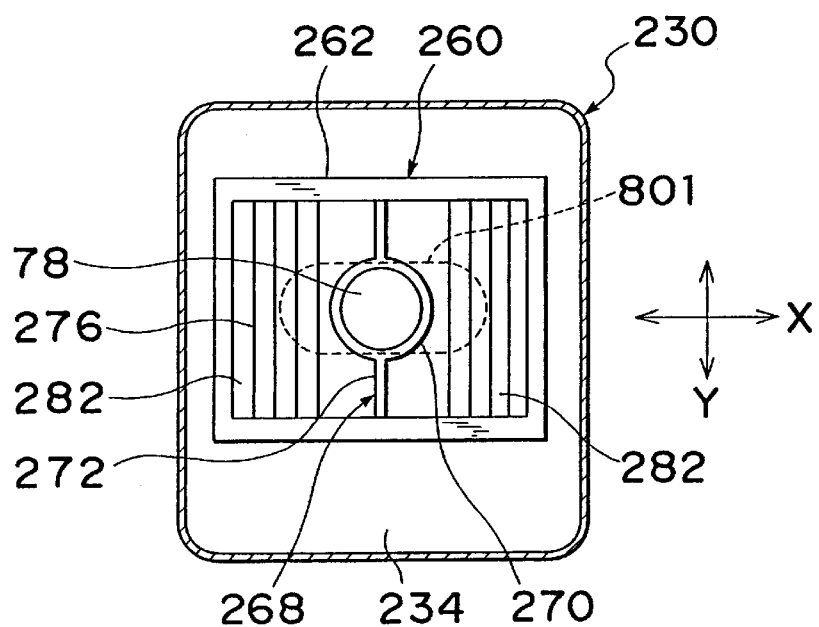
FIG. 38 is a plan view of a third embodiment of a blind.
Figure 39:
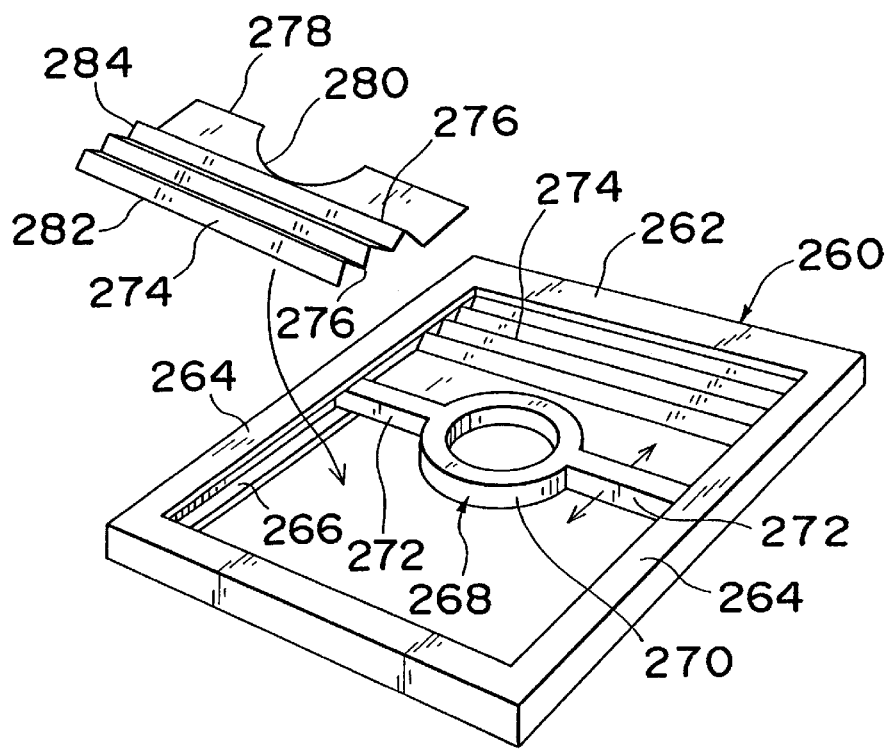
FIG. 39 is a perspective view of the blind shown in FIG. 38.

FIGS. 38 and 39 show another embodiment of the blind generally indicated by reference numeral 260. The blind 260 includes a rectangular frame 262 fixed on the cover plate 232 or 234. A pair of opposing members 264 of the frame 262 is formed at opposing surfaces thereof with longitudinal grooves 266 (one of which being shown in the drawing), respectively. A bar or slider 268, formed at a mid-portion thereof with a ring 270 having an inner diameter slightly larger than the outer diameter of the shaft 78, is arranged in the frame 262 with opposite ends thereof slidably engaged in the grooves 266. A pair of rectangular folding sheets 274 are prepared to cover spaces located on both sides of the slider 268, respectively. Each folding sheet 274 is made from a plastic film or metal film and has a plurality of equally spaced folds 276 each extending perpendicular to a sliding direction of the slider 268. Also, each folding sheet 274 is formed at one end opposing to the slider 268 with a semicircle cutout 280 that corresponds to a contour of the ring 270. Each folding sheet 274 so formed is fixed so that the cutout 280 engages with the corresponding peripheral portion of the ring 270. Also, one pair of opposing edges 284 having ends of the folds 276 ends are engaged in the grooves 266, while another pair of opposing edges 278 and 282 are bonded to the corresponding portions of slider 268 and frame 262, respectively.

With this arrangement, in response to the movement of the shaft 78 along the opening 80, the slider 268 moves in the same direction. This causes the folding sheets 274 to expand and contract with covering the opening 801.

Although each table of the X/Y-transport mechanism includes lead screws and associated nuts whereby a lead screw is threaded for converting the rotation transmitted from a motor into linear movement, the mechanism for moving the table is not limited thereto. For example, another mechanism which uses belts or chains can be employed instead.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. An X-ray apparatus, comprising:

a first frame having a support and a patient positioning station, said support being spaced away from said patient positioning station;

a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;

a revolving shaft which is fixed at a first end thereof to said second moving member;

a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;

a rotating mechanism having a drive source which rotates said second frame relative to said first frame about said revolving shaft; and a controller which drives at least one of said moving mechanism and said rotating mechanism according to a digital signal transmitted to said controller, wherein said moving mechanism is designed so that said second frame takes a first position where said X-ray generator opposes said X-ray receiver through the head of a patient positioned in said patient positioning station and a second position where said X-ray generator and said X-ray receiver are positioned so that an operator of said X-ray apparatus is able to look at the head of said patient positioned in said patient positioning station from a side view.

2. An X-ray apparatus as claimed in claim 1, wherein said second frame in said second position permits said patient to approach said patient positioning station without interference from said second frame.

3. An X-ray apparatus as claimed in claim 1, wherein said X-ray generator and said X-ray receiver of said second frame in said second position are displaced substantially in one of two areas divided by a median line of said patient positioned in said patient positioning station.

4. An X-ray apparatus as claimed in claim 1, wherein said X-ray generator and said X-ray receiver of said second frame in said second position are displaced substantially behind said patient positioned in said patient positioning station.

5. An X-ray apparatus as claimed in claim 1, further comprising:

a connector which includes a shaft connector which connects said revolving shaft to said second frame so that said revolving shaft moves relative to said second frame in a third direction perpendicular to a longitudinal axis of said revolving shaft; and a second transport mechanism which transports said revolving shaft in said third direction relative to said second frame.

6. An X-ray apparatus as claimed in claim 1, wherein said X-ray receiver includes:

a guide extending substantially perpendicularly to said revolving shaft;

a cassette capable of being guided by said guide; and a drive source which moves said cassette along said guide.

7. An X-ray apparatus, comprising:

a first frame having a support and a patient positioning station, said support being spaced away from said patient positioning station;

a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;

a revolving shaft which is fixed at a first end thereof to said second moving member;

a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;

a rotating mechanism having a drive source which rotates said second frame relative to said first frame about said revolving shaft; and a controller which drives at least one of said moving mechanism and said rotating mechanism according to a digital signal transmitted to said controller, wherein said moving mechanism is designed so that said second frame takes a first position where said X-ray generator opposes said X-ray receiver through the head of a patient positioned in said patient positioning station and a second position where an area between said X-ray generator and said X-ray receiver is located substantially outside the head of said patient positioned in said patient positioning station.

8. An X-ray apparatus as claimed in claim 7, wherein said second frame in said second position permits said patient to approach said patient positioning station without interference from said second frame.

9. An X-ray apparatus as claimed in claim 7, wherein said X-ray generator and said X-ray receiver of said second frame in said second position are displaced substantially in one of two areas divided by a median line of said patient positioned in said patient positioning station.

10. An X-ray apparatus as claimed in claim 7, wherein said X-ray generator and said X-ray receiver of said second frame in said second position are displaced substantially behind said patient positioned in said patient positioning station.

11. An X-ray apparatus as claimed in claim 7, further comprising:

a connector which includes a shaft connector which connects said revolving shaft to said second frame so that said revolving shaft moves relative to said second frame in a third direction perpendicular to a longitudinal axis of said revolving shaft; and a second transport mechanism which transports said revolving shaft in said third direction relative to said second frame.

12. An X-ray apparatus as claimed in claim 7, wherein said X-ray receiver includes:
- a guide extending substantially perpendicularly to said revolving shaft;
- a cassette capable of being guided by said guide; and
- a drive source which moves said cassette along said guide.

13. An X-ray apparatus, comprising:
- a first frame having an opening;
- a transport mechanism mounted on said first frame, said transport mechanism including a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;
- a revolving shaft which is fixed at a first end thereof to said second moving member;
- a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;
- a rotating mechanism having a drive source which rotates said second frame relative to said first frame about said revolving shaft;
- a control which drives at least one of said moving mechanism and said rotating mechanism according to a digital signal transmitted to said controller; and
- a blind which covers said opening when said revolving shaft moves.

14. An X-ray apparatus as claimed in claim 13, wherein said blind includes:
- a ring rotatably mounted around said revolving shaft;
- a frame fixed on said first frame for covering said opening; and
- an extensible sheet member which connects said ring and said first frame.

15. An X-ray apparatus as claimed in claim 13, further comprising:
- a pivot extending substantially parallel to said revolving shaft; and
- a blind member rotatably supported by said first or second frame about said pivot for covering said opening of said first frame with the movement of said revolving shaft relative to said first frame.

16. An X-ray apparatus, comprising:
- a first frame having a patient positioning station;
- a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;
- a revolving shaft which is fixed at a first end thereof to said second moving member;
- a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;
- a rotating mechanism having a drive source which rotates said second frame relative to said first frame about said revolving shaft; and
- a controller which drives at least one of said moving mechanism and said rotating mechanism according to a digital signal transmitted to said controller, wherein
- said first frame includes a first portion extended in one direction and a second portion extended in another direction angled with said one direction,
- said transport mechanism is mounted on said second portion, and
- said X-ray generator and said X-ray receiver of said second frame in said second position are displaced substantially behind a patient positioned in said patient positioning station.

17. An X-ray apparatus, comprising:
- a first frame;
- a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;
- a revolving shaft which is fixed at a first end thereof to said second moving member;
- a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;
- a rotating mechanism having a drive source which rotates said second frame relative to said first frame about said revolving shaft;
- a controller which drives at least one of said moving mechanism and said rotating mechanism according to a digital signal transmitted to said controller;
- a connector which includes a shaft connector which connects said revolving shaft to said second frame so that said revolving shaft moves relative to said second frame in a third direction perpendicular to a longitudinal axis of said revolving shaft; and
- a second transport mechanism which transports said revolving shaft in said third direction relative to said second frame, wherein
- said first frame includes a first portion extended in one direction and a second portion extended in another direction angled with said one direction, and said transport mechanism is mounted on said second portion.

18. An X-ray apparatus, comprising:

a first frame;

a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;

a revolving shaft which is fixed at a first end thereof to said second moving member;

a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;

a rotating mechanism having a drive source which rotates said second frame relative to said first frame about said revolving shaft;

a controller which drives at least one of said moving mechanism and said rotating mechanism according to a digital signal transmitted to said controller;

a rotating shaft which extends parallel to said revolving shaft and rotatably connects said X-ray receiver to said second frame;

a motor mounted on said second frame; and a transmission which, by means of a drive, connects said rotating shaft and said motor so that upon driving of said motor said X-ray receiver is rotated about said rotating shaft relative to said second frame, wherein said motor is located on a first side of said rotating shaft away from said X-ray generator, and said transmission includes a rotating member connected by a drive with said motor and a changeover device for changing a rotation of said rotating shaft to another rotation of said X-ray receiver about said rotating shaft.

19. An X-ray apparatus, comprising:

a first frame mounted on a floor or a wall of a X-ray chamber, said first frame being constrained not to move horizontally;

a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;

a revolving shaft which is fixed at a first end thereof to said second moving member;

a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;

a rotating mechanism having a drive source which rotates said second frame relative to said first frame about said revolving shaft;

a controller which drives at least one of said moving mechanism and said rotating mechanism according to a digital signal transmitted to said controller;

a second X-ray receiver, for use in a cephalogram, vertically spaced apart from said first frame;

a holding member for holding said second X-ray receiver;

a displacing mechanism which displaces said first X-ray receiving surface from between said X-ray source and said second X-ray receiving surface;

a switch for changing between a cephalometric photographing mode which uses said second X-ray receiver and another photographing mode, different from said cephalometric photographing mode, which uses said first X-ray receiver; and a controller which drives said transport mechanism to displace said X-ray generator to a position farthest from said second X-ray receiver with respect to said first or second direction when said cephalometric photographing mode is selected.

20. An X-ray apparatus as claimed in claim 19, wherein said holding member includes a revolving arm which extends horizontally from said first frame and carries said second X-ray receiver at a distal end thereof.

21. An X-ray apparatus as claimed in claim 19, wherein said holding member includes a wall of an X-ray chamber in which said X-ray apparatus is installed.

22. An X-ray apparatus as claimed in claim 19, wherein said displacing mechanism includes:

a rotating shaft for rotatably supporting said X-ray generator relative to said second frame about an axis parallel to said revolving shaft; and a drive source for rotating said X-ray generator about said rotating shaft.

23. An X-ray apparatus as claimed in claim 19, wherein said displacing mechanism includes:

a rotating shaft for rotatably supporting said first X-ray receiver relative to said second frame about an axis parallel to said revolving shaft; and a drive source for rotating said X-ray generator about said rotating shaft.

24. An X-ray apparatus, comprising:

a first frame;

a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;

a revolving shaft which is fixed at one first end thereof to said second moving member;

a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;

a rotating mechanism having a drive source which rotates said second frame relative to said first frame about said revolving shaft;

a controller which drives at least one of said moving mechanism and said rotating mechanism according to a digital signal transmitted to said controller;

a rotating shaft which extends parallel to said revolving shaft and rotatably connects said X-ray receiver to said second frame;

a motor mounted on said second frame for rotating said X-ray receiving surface relative to a direction in which an X-ray is transmitted; and a transmission which, by means of a drive, connects said rotating shaft and said motor so that upon driving of said motor said X-ray receiver is rotated about said rotating shaft relative to said second frame.

25. An X-ray apparatus as claimed in claim 24, further comprising:

a patient positioning station, and a linear tomogram mode in which a longitudinal cross section or a transverse cross section of a dentition of a patient positioned in said patient positioning station is photographed.

26. An X-ray apparatus as claimed in claim 24, further comprising: a second controller for rotating said X-ray receiver relative to said second frame while keeping said X-ray receiving surface substantially parallel to said photographing cross section when in said linear cross section photographing mode.

27. An X-ray apparatus as claimed in claim 24, wherein said motor is located on a first side of said rotating shaft away from said X-ray generator.

28. An X-ray apparatus, comprising:

a first frame having a patient positioning station;

a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;

a revolving shaft which is fixed at a first end thereof to said second moving member;

a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;

a rotating mechanism having a drive source which rotates said second frame relative to said first frame about said revolving shaft; and a controller which drives at least one of said moving mechanism and said rotating mechanism according to a digital signal transmitted to said controller, wherein said first frame includes a first portion extended in one direction and a second portion extended in another direction angled with said one direction, said transport mechanism is mounted on said second portion, and said second frame in said second position permits a patient to approach said patient positioning station without interference from said second frame.

29. An X-ray apparatus, comprising:

a first frame having a patient positioning station;

a transport mechanism mounted on said first frame, said transport mechanism including: a first guide extending in a first direction, a first moving member supported by said first guide member so that it can move along said first guide, a first drive source which moves said first moving member along said first guide, a second guide fixedly supported on said first moving member and extended in a second direction which crosses at a certain angle with said first direction, a second moving member supported by said second guide member so that it can move along said second guide, and a second drive source which moves said second moving member along said second guide;

a revolving shaft which is fixed at a first end thereof to said second moving member;

a second frame having an X-ray generator with an X-ray source and an X-ray receiver with an X-ray receiving surface spaced away from said X-ray generator, said second frame being supported at a portion located between said X-ray generator and said X-ray receiver by a second end of said revolving shaft;

a rotating mechanism having a drive source which rotates said second frame relative to said first frame about said revolving shaft; and a controller which drives at least one of said moving mechanism and said rotating mechanism according to a digital signal transmitted to said controller, wherein said first frame includes a first portion extended in one direction and a second portion extended in another direction angled with said one direction, said transport mechanism is mounted on said second portion, and said X-ray generator and said X-ray receiver of said second frame in said second position are displaced substantially in one of two areas divided by a median line of a patient positioned in said patient positioning station.

* * * * *